United States Patent [19]

Nomura et al.

[11] Patent Number: 5,223,620

[45] Date of Patent: Jun. 29, 1993

[54] PYRIDO[2,3-D]PYRIMIDINE COMPOUNDS USEFUL AS INTERMEDIATES

[75] Inventors: Hiroaki Nomura, Osaka; Hiroshi Akimoto; Tetsuo Miwa, both of Kobe, all of Japan

[73] Assignee: Takeda Chemical Industries, Ltd., Osaka, Japan

[21] Appl. No.: 830,884

[22] Filed: Feb. 4, 1992

Related U.S. Application Data

[63] Continuation of Ser. No. 521,572, May 10, 1990, abandoned, which is a continuation of Ser. No. 329,374, Mar. 27, 1989, Pat. No. 4,946,846.

[30] Foreign Application Priority Data

Apr. 1, 1988 [JP] Japan .................................. 63/82043
Feb. 6, 1989 [JP] Japan .................................. 1/28120

[51] Int. Cl.⁵ .......................................... C07D 471/04
[52] U.S. Cl. .................................................. 544/279
[58] Field of Search ................ 544/279, 287, 291, 292

[56] References Cited

U.S. PATENT DOCUMENTS

| | | | |
|---|---|---|---|
| 4,460,591 | 7/1984 | DeGraw et al. | 544/279 |
| 4,684,653 | 8/1987 | Taylor et al. | 514/258 |
| 4,725,687 | 2/1988 | Piper et al. | 544/279 |

FOREIGN PATENT DOCUMENTS

| | | | |
|---|---|---|---|
| 0031237 | 7/1981 | European Pat. Off. | 544/279 |
| 0075880 | 4/1983 | European Pat. Off. | 544/279 |
| 0248573 | 12/1987 | European Pat. Off. | 544/279 |
| 0255228 | 2/1988 | European Pat. Off. | 544/279 |

OTHER PUBLICATIONS

Bianchi, "1-Pharmacology," *Chemical Abstracts*, vol. 103, No. 1, pp. 607, 668 (1985).
Chemical Abstracts vol. 103, No. 1, Abstract 6676, p. 607, 1985, Taylor et al.
Hynes et al., "Synthesis of Quinazoline Analogs of Isofolic Acid," *Journal of Medicinal Chemistry*, vol. 18, No. 6, pp. 632–634 (1975).
Taylor et al., "Synthesis of the Antileukemic Agents 5, . . . ", *Journal of Medicinal Chemistry*, vol. 28, pp. 914–921 (1985).

*Primary Examiner*—C. Warren Ivy
*Assistant Examiner*—Zinna N. Davis
*Attorney, Agent, or Firm*—Wegner, Cantor, Mueller & Player

[57] ABSTRACT

New fused pyrimidines of the general formula (I):

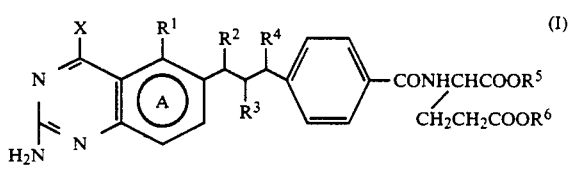

wherein the ring (A) is a pyridine ring which may be hydrogenated or a benzene ring which may be hydrogenated, X is an amino group or a hydroxyl group, $R^1$, $R^2$, $R^3$ and $R^4$ are independently hydrogen, fluorine or a lower alkyl group, and $-COOR^5$ and $-COOR^6$ are independently a carboxyl group which may be esterified, and salts thereof have excellent anti-tumor effects, and they can be produced by the following reaction scheme:

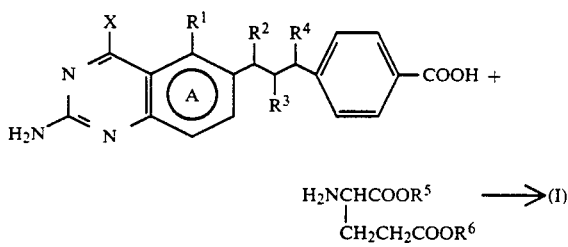

in which (A) is, X, $R^1$ to $R^4$, $-COOR^5$ have the above meanings.

1 Claim, No Drawings

PYRIDO[2,3-D]PYRIMIDINE COMPOUNDS USEFUL AS INTERMEDIATES

This application is a continuation of Ser. No. 07/521,572 filed May 10, 1990 (now abandoned), which in turn is a continuation of Ser. No. 329,374 filed Mar. 27, 1989 (now U.S. Pat. No. 4,946,846).

This invention relates to novel fused pyrimidine derivatives which are useful as anti-tumor agents, the method of production thereof and their use.

Folic acid is a carrier of a C1 unit derived from formic acid or formaldehyde, acting as a coenzyme in various enzymatic reactions such as those involved in the biosynthesis of nucleic acids, in the metabolism of amino acids and peptides, and in the generation of methane. Particularly in the biosynthesis of nucleic acids, folic acid is essential for formylation in the two pathways, i.e. the purine synthetic pathway and the thymidine synthetic pathway. Usually folic acid is required to be transformed into its activated coenzyme form by reduction in two steps before it becomes biologically active. Amethopterin (methotrexate:MTX) and its related compounds are known to inhibit the reduction from dihydrofolic acid into tetrahydrofolic acid by coupling strongly with the dominant enzyme in the second step (dihydrofolic acid reductase). These drugs have been developed as anti-tumor drugs because they may disturb the DNA synthesis and consequently cause cell death, and are regarded of major clinical importance now. On the other hand, a novel tetrahydroaminopterin anti-tumor agent (5,10-dideaza-5,6,7,8-tetrahydroaminopterin: DDATHF) has been reported which, unlike the drugs described above, does not inhibit dihydrofolic acid reductase and of which the main mechanism consists in the inhibition of glycinamide ribonucleotide transformylase required in the initial stage of purine biosynthesis [Journal of Medicinal Chemistry, 28, 914 (1985)].

Various studies are now being conducted on therapy for cancer, and what is expected strongly is the development of drugs which are more effective and have toxicities highly specific to cancer cells based on some new mechanism. The anti-tumor agent MTX, the active mechanism of which consists in an antagonism towards folic acid, is clinically used, although its therapeutic effect is still unsatisfactory because it has a relatively strong toxicity with little effect on solid cancer. It is also a major problem that cancer cells acquire tolerance towards the agent (MTX).

We have now discovered that novel fused pyrimidine derivatives having a trimethylene chain have toxicities which are highly specific to tumor cells and excellent anti-tumor effects. The present invention is based on this discovery.

This invention consists in (1) a compound of the general formula (I):

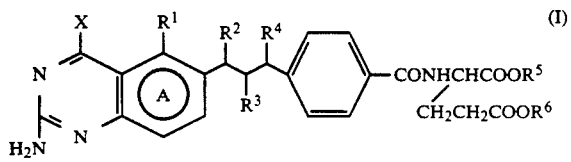

wherein the ring Ⓐ is a pyridine ring which may be hydrogenated or a benzene ring which may be hydrogenated, X is an amino group or a hydroxyl group, $R^1$, $R^2$, $R^3$ and $R^4$ are independently hydrogen, fluorine or a lower alkyl group, and $-COOR^5$ and $-COOR^6$ are independently a carboxyl group which may be esterified, or a salt thereof; (2) a process for producing a compound (I) as defined above which is characterized by reacting a compound of the general formula (II):

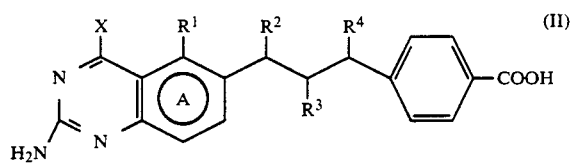

wherein the ring Ⓐ, X, $R^1$, $R^2$, $R^3$ and $R^4$ are as defined above in relation to (I), or a reactive derivative at the carboxyl group or a salt thereof, with a compound of the general formula (III):

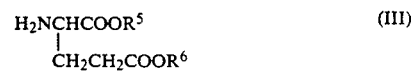

wherein $-COOR^5$ and $COOR^6$ are as defined above in relation to (I), or a salt thereof;

(3) a compound of the general formula (IV):

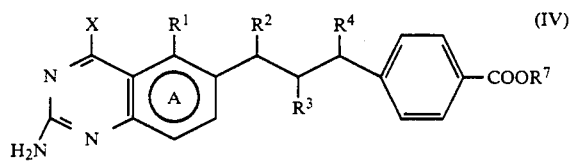

wherein the ring Ⓐ, X, $R^1$, $R^2$, $R^3$ and $R^4$ are as defined above in relation to (I), and $-COOR^7$ is a carboxyl group which may be esterified; or a salt thereof; and (4) an anti-tumor agent containing a compound (I) as defined above or a pharmaceutically acceptable salt thereof; and (5) the use of a compound (I) as defined above, or a pharmaceutically acceptable salt thereof in the preparation of a medicine for anti-tumor or cancer therapy.

When X in the formulae shown and defined above is a hydroxyl group, each of the compounds (I), (II), and (IV) may exist as an equilibrium mixture of the respective tautomers. The following partial structural formulae show the site of the structure which is subject to tautomerism, and the equilibrium between the tautomers is illustrated as follows:

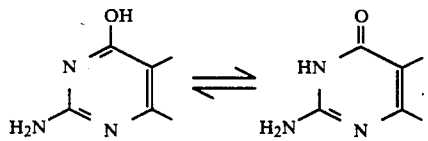

For convenience of description, only the hydroxy forms and the corresponding names are used throughout this specification, but the corresponding oxo forms are always included.

There may be two or more asymmetric centers in the compounds (I) of this invention, and the absolute configuration at all of the asymmetric carbon atoms may be S, R, or an S-R mixed form, except that the absolute configuration at the asymmetric carbon atom in the side chain derived from glutamic acid is always S(L). Therefore, the compounds (I) may have two or more diastereomers which, if necessary, can easily be separated from each other by a routine method for separation and purification. All of the diastereomers which can be separated by such a method are included within this invention.

The pyridine ring which may be hydrogenated, represented inter alia by the ring (A) in the above formulae may be either pyridine or tetrahydropyridine. Furthermore, the benzene ring which may be hydrogenated, also represented by the ring (A), may be benzene, cyclohexene or 1,3-cyclohexadiene. Preferable examples of the ring (A) include a pyridine ring which may be hydrogenated such as pyridine or tetrahydropyridine, and more preferred examples include tetrahydropyridine.

The term "lower alkyl group", represented inter alia by $R^1$, $R^2$, $R^3$ and $R^4$ in the above formulae, includes an alkyl group having 1 to 3 carbon atoms (e.g., methyl, ethyl, propyl or isopropyl).

An esterified carboxyl group in a carboxyl group which may be esterified, represented by $-COOR^5$, $-COOR^6$ and $-COOR^7$, includes a carboxyl group esterified by (i) a lower alkyl group having 1 to 5 carbon atoms, (ii) a benzyl group which may be substituted, preferably with one or two of the nitro groups or a lower alkoxy group having 1 to 3 carbon atoms e.g., methoxy, ethoxy), or (iii) a phenyl group which may be substituted, preferably with one or two of the nitro groups or a lower alkoxy group having 1 to 3 carbon atoms (e.g., methoxy, ethoxy or propoxy).

The term "lower alkyl group" includes methyl, ethyl, propyl, isopropyl, n-butyl, iso-butyl, sec-butyl, tert-butyl, n-pentyl, iso-pentyl, sec-pentyl, neo-pentyl and tert-pentyl. The expression "benzyl group which may be substituted" includes benzyl, nitrobenzyl and methoxybenzyl. The expression "phenyl group which may be substituted" includes phenyl, nitrophenyl and methoxyphenyl.

Preferred examples of $R^1$ include hydrogen and an alkyl group having 1 to 3 carbon atoms, and more preferable ones include hydrogen.

Preferred examples of each of $R^2$, $R^3$, $R^4$, $R^5$ and $R^6$ include hydrogen.

Preferred examples of X include an amino group.

In the following partial structural formula of the compounds (I), (II) and (IV);

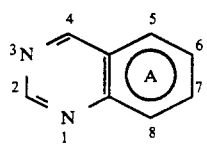

where the ring (A) is a pyridine ring which may be hydrogenated, $R^1$ is preferably at the 5-position thereof and the trimethylene side chain

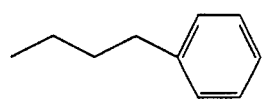

is preferably attached to the fused structure

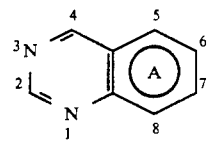

at the 6-position thereof, respectively.

Preferred examples of the compound (I) and its salt include a compound of the general formula:

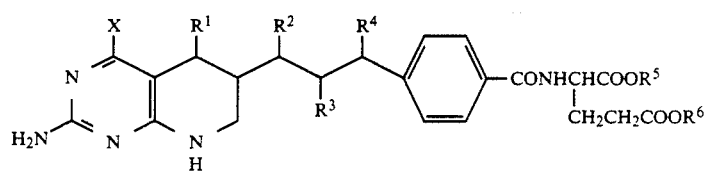

wherein the symbols X, $R^1$, $R^2$, $R^3$, $R^4$, $R^5$ and $R^6$ are as defined above and a pharmaceutically acceptable salt thereof.

The compounds (I) or their salts (as described hereinafter) can be obtained by acylation of glutamic acid derivatives (III) or salts thereof (as described in those of the compound (I)) with the carboxylic acids (II) or reactive derivatives or salts (as described in those of the compound (I)) thereof. Acylation may be performed for example by acylation of the compound (III) or a salt thereof with the compound (II) or a salt thereof in the presence of a carbodiimide. In general about 1 to 20 mole equivalents, preferably 1 to 5 mole equivalents of the compound (III) or its salt relative to the compound (II) or its salt is used. Generally about 1 to 25 mole equivalents, preferably about 1 to 5 mole equivalents of a carbodiimide relative to the compound (II) or its salt is used.

As the carbodiimide, dicyclohexyl-carbodiimide is preferred for practical reasons, but other carbodiimides such as diphenylcarbodiimide, di-o-tolylcarbodiimide, di-p-tolylcarbodiimide, di-tert-butylcarbodiimide, 1-cyclohexyl-3-(2-morpholinoethyl)carbodiimide, 1-cyclohexyl-3-)4-diethylaminocyclohexyl)carbodiimide, 1-ethyl-3-(2-diethylaminopropyl)carbodiimide and 1-ethyl-3-(3-diethylaminopropyl)carbodiimide may be used in the alternative.

The acylation is preferably performed in the presence of a suitable solvent, and such solvents include esters (e.g., ethyl acetate), ethers (e.g. dimethyl ether, diethyl ether, tetrahydrofuran, dioxane, monoglyme, diglyme), halogenated hydrocarbons (e.g. dichloromethane, chloroform, carbon tetrachloride), nitriles (e.g. acetonitrile), aromatic hydrocarbons (e.g. benzene, toluene, xylene), nitromethane, pyridine, dimethylformamide, dimethylsulfoxide, hexamethylphospholamide and suitable mixtures of these solvents.

The reaction is allowed to proceed generally at a pH ranging from 2 to 14, preferably at a pH ranging from about 6 to 9, at a temperature ranging from about $-10°$ C. to the boiling point of the solvent used (up to about 100° C.), preferably at a temperature ranging from about 0° to 50° C., for about 1 to 100 hours.

The acylation reaction proceeds more advantageously in the presence of a catalyst which promotes acylation. Such catalysts include base catalysts and acid catalysts. The base catalysts include tertiary amines (e.g. aliphatic tertiary amines such as triethylamine; aromatic tertiary amines such as pyridine, α-, β- or γ-picoline, 2,6-lutidine, 4-dimethyl-aminopyridine, 4-(1pyrrolidinyl)pyridine, di-methylaniline and diethylaniline), and such acid catalysts include Lewis acids [e.g. anhydrous zinc chloride, anhydrous aluminum chloride ($AlCl_3$), anhydrous ferric chloride, titanium tetrachloride ($TiCl_4$), tin tetrachloride ($SnCl_4$), antimony pentachloride, cobalt chloride, cupric chloride or boron trifluoride ethyl ether complex], strong inorganic acids (e.g. sulfuric acid, perchloric acid, hydrogen chloride, hydrogen bromide, etc.), strong organic acids (e.g. benzenesulfonic acid, p-toluenesulfonic acid, trifluoroacetic acid or trichloro-acetic acid) and acidic ion-exchange resins (e.g. polystylenesulfonic acid). Among the catalysts described above, 4-dimethylaminopyridine or 4-(1-pyrrolidinyl)-pyridine is preferable in many cases. A suitable amount of the catalyst is an amount sufficient to promote acylation, generally about 0.01 to 10 mole equivalents, preferably about 0.1 to 1 mole equivalents relative to the compound (II) or a salt thereof. The reactive derivatives of carboxylic acids (II) at the carboxyl group, used for the acylation at the carboxyl group in the carboxylic acid include acid halides (e.g. fluoride, chloride, bromide, iodide), acid anhydrides (e.g. iodoacetic acid anhydride, isobutyric acid anhydride), mixed acid anhydrides with mono-lower alkylcarbonic acid esters (e.g. monomethylcarbonic acid ester, monoethylcarbonic acid ester, monopropylcarbonic ester, mono-iso-propylcarbonic acid ester, monobutylcarbonic acid ester, mono-iso-butylcarbonic acid butylcarbonic acid ester, mono-sec ester or mono-tert-butylcarbonic acid ester), active esters (e.g. cyanomethyl ester, carboethoxymethyl ester, methoxymethyl ester, phenyl ester, o-nitrophenyl ester, p-nitrophenyl ester, p-carbomethoxyphenyl ester, p-cyanophenyl ester or thiophenyl ester), acid azides, mixed acid anhydrides with phosphoric acid diesters (e.g. dimethyl phosphate, diethyl phosphate, dibenzylphosphate, diphenylphosphate), and mixed acid anhydrides with phosphorous acid diesters (e.g. dimethyl phosphite, diethyl phosphite, dibenzyl phosphite or diphenyl phosphite), of the carboxylic acid (II), as produced in the conventional manner.

For acylation with such a reactive derivative of (II), the solvent, the catalyst and the reaction temperature are the same as those for acylation in the presence of a carbodiimide as described above.

For the production of the compound (I-1) or its salt in which —$COOR^5$ and —$COOR^6$ in the compound (I) or its salt thereof are carboxyl groups, it is desirable that the compound (III) or its salt in which —$COOR^5$ and —$COOR^6$ are esterified carboxyl groups be allowed to react with the compound (II) or its reactive derivative or its salt: this is followed by deesterification by means of a conventional degradation or catalytic reduction reaction.

Such degradation can be performed by hydrolysis under basic conditions (method A), hydrolysis under acidic conditions (method B-1) or hydrolysis under acidic non-aqueous conditions (method B-2). Bases used in the method A include metal alkoxides such as sodium methoxide, sodium ethoxide, sodium butoxide and potassium butoxide, metal hydroxides such as sodium hydroxide, potassium hydroxide, lithium hydroxide and barium hydroxide, and amines such as ammonia, triethylamine and pyridine. Acids used in the method B-1 include mineral acids such as hydrochloric acid, hydrobromic acid, sulfuric acid, nitric acid and phosphoric acid, and organic acids such as trifluoroacetic acid, trichloroacetic acid, methane-sulfonic acid, benzenesulfonic acid, p-toluenesulfonic acid and camphorsulfonic acid. Catalysts used in the method B-2 include mineral acids such as hydrogen chloride, hydrogen bromide, perchloric acid, sulfuric acid nitric acid and phosphoric acid, organic acids such as trifluoroacetic acid, trichloroacetic acid, methanesulfonic acid, benzenesulfonic acid, p-toluenesulfonic acid and camphorsulfonic acid, and Lewis acids such as anhydrous zinc chloride, anhydrous aluminum chloride ($AlCl_3$), anhydrous ferric chloride, titanium tetrachloride ($TiCl_4$), tin tetrachloride ($SnCl_4$), antimony pentachloride, cobalt chloride, cupric chloride and boron trifluoride ethyl ether complex. Degradation is performed in a suitable solvent at a temperature ranging from 0° C. to the boiling point of the solvent, preferably at 10° to 80° C., for 30 minutes to 2 days. The solvent used for the reaction by the method A or by the method B-1 may be water, methanol, ethanol, propanol, butanol, ethyleneglycol, methoxyethanol, ethoxyethanol, tetrahydrofuran, dioxane, monoglyme, diglyme, pyridine, dimethylformamide, dimethylsulfoxide or sulfolane, or a suitable mixture of two or more of these solvents; the solvent used for the reaction by the method B-2 may be ethyl acetate, dimethyl ether, diethyl ether, tetrahydrofuran, dioxane, monoglyme, diglyme, dichloromethane, chloroform, carbon tetrachloride, acetonitrile, benzene, toluene, xylene, nitromethane or pyridine, or a suitable mixture of two or more of these solvents.

Such catalytic reduction (method C) is performed in a suitable solvent at a temperature ranging from about −40° C. to the boiling point of the solvent used, preferably at about 0° to 50° C. The solvents used include water, alcohols (e.g. methanol, ethanol, propanol, isopropanol, butylalcohol, sec-butylalcohol, tert-butylalcohol, ethoxyethanol), acetic acid esters (e.g. methyl acetate, ethyl acetate), ethers (e.g. dimethyl ether, diethyl ether, tetrahydrofuran, dioxane, monoglyme, diglyme), aromatic hydrocarbons (e.g. benzene, toluene, xylene), pyridine, dimethylformamide, and suitable mixtures of two or more of these solvents. Catalysts for the catalytic reaction include palladium, platinum, rhodium and Raney nickel. The addition of a trace amount of acetic acid, trifluoroacetic acid, hydrochloric acid or sulfuric acid allows the reaction to proceed more advantageously.

The method for the production of the compound (I-1) or a salt thereof is selected according to the nature of the —$COOR^5$ and —$COOR^6$ group; when —$COOR^5$ and —$COOR^6$ are carboxyl groups esterified with a methyl, ethyl, propyl, butyl, sec-butyl, phenyl or substituted phenyl group, the method A or the method B-1 is applied advantageously; when —$COOR^5$ and —$COOR^6$ are carboxyl groups esterified with a iso-propyl or tert-butyl group, the method B-2 is applied; and when —$COOR^5$ and —$COOR^6$ are carboxyl groups esterified with a benzyl or a substituted benzyl group, the method B-1 or the method C is applied advantageously. When —$COOR^5$ and —$COOR^6$ are different from each other, the methods A, B-1, B-2 and C may be combined appropriately.

In the following the methods for production of the starting compounds (II) and (III) or salts thereof are explained.

The compound (II) wherein the ring Ⓐ is a pyridine ring which may be hydrogenated, or a salt thereof may be produced for example by the following processes.

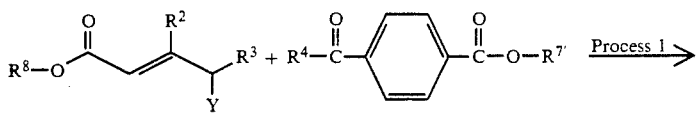

Compound (V)        Compound (VI)

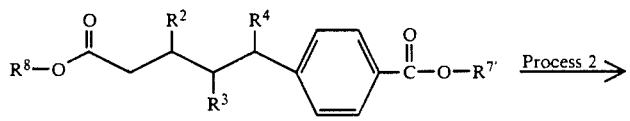

Compound (VII)

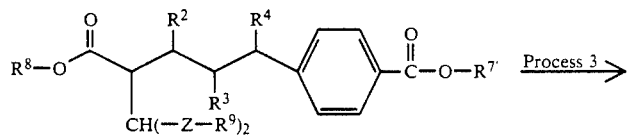

Compound (VIII)

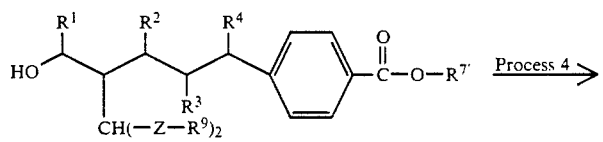

Compound (IX)

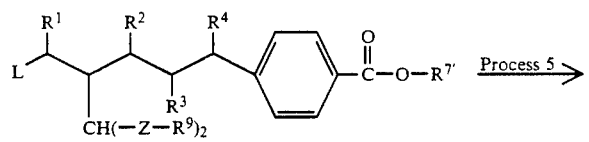

Compound (X)

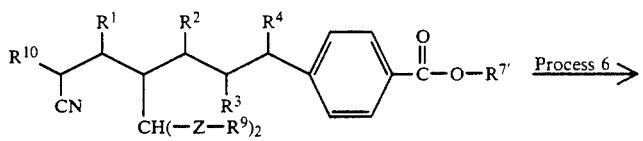

Compound (XI)

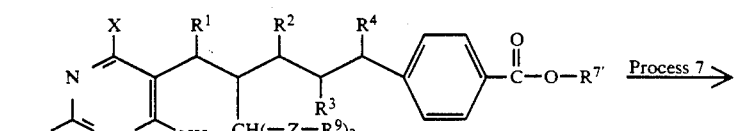

Compound (XII)

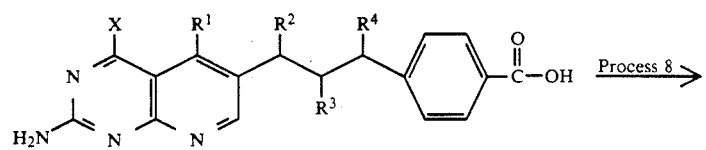

Compound (II-1)

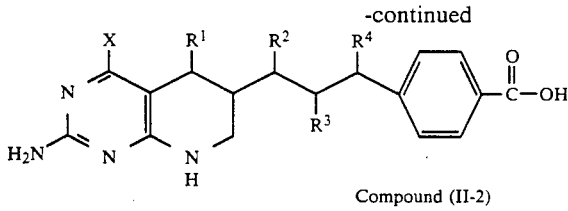

Compound (II-2)

In the reaction formulae described above, X, $R^1$, $R^2$, $R^3$ and $R^4$ are the same as described above; L is a halogen atom (e.g. chlorine, bromine or iodine atom), an eliminatable group which may be easily derived from a hydroxy group (e.g. methanesulfonyloxy group, benzenesulfonyloxy group, p-toluenesulfonyloxy group or trifluoromethane-sulfonyl group) or a carboxylic acid ester (e.g. acetoxy or benzoyloxy); Y is hydrogen or a halogen atom (e.g. fluorine, chlorine, bromine or iodine, etc.), Z is an oxygen atom or sulfur atom; —$COOR^7$ is an esterified carboxyl group; $R^8$ and $R^{10}$ are independently a lower alkyl group having 1 to 4 carbon atoms (e.g. methyl, ethyl, propyl, isopropyl, butyl, sec-butyl or tertbutyl,), benzyl or a substituted benzyl group (p-nitrobenzyl or p-methoxy-benzyl), or phenyl or a substituted phenyl group (e.g. p-nitrophenyl or p-methoxyphenyl); $R^9$ is a lower alkyl group having 1 to 4 carbon atom(s), benzyl or a substituted phenyl group as mentioned above. The esterified carboxyl group represented by —$COOR^7$ is exemplified by such esterified carboxyl group as in "the carboxyl group which may be esterified" represented by —$COOR^7$.

The compound (XII) may include an acid addition salt as mentioned hereinafter in relation to salts of the compound (I).

In the following, the reaction processes described above are explained in detail.

Process 1

The compound (V) and the compound (VI) are subjected to condensation (aldol reaction, Wittig reaction or Reformatsky reaction) and then to catalytic reduction under hydrogen atmosphere to obtain the compound (VII).

In the condensation by aldol reaction, the employable base catalysts include metal hydroxides such as sodium hydroxide, potassium hydroxide, lithium hydroxide and barium hydroxide, metal alkoxides such as sodium methoxide, sodium ethoxide and potassium tert-butoxide, metal amides such as sodium amide and lithium diisopropylamide, metal hydrides such as sodium hydride and potassium hydride, organic metal compounds such as phenyllithium and butyllithium, and amines such as triethylamine, pyridine, α-, β- or γ-picoline, 2,6-lutidine, 4-dimethylaminopyridine, 4-(1-pyrrolidinyl)pyridine, dimethylaniline and diethylaniline; the employable acid catalysts include mineral acids such as hydrochloric acid, sulfuric acid, nitric acid, phosphoric acid and boric acid, and organic acids such as oxalic acid, tartaric acid, acetic acid, trifluoroaceitc acid, methanesulfonic acid, benzenesulfonic acid, p-toluenesulfonic acid and camphorsulfonic acid. The condensation can be conducted according to a known method [Ei-Ichi Negishi, Organometallics in Organic Synthesis, vol 1, John Wiley & Sons, New York, Chichester, Brisbane, Toronto (1980)] which comprises converting a ketone form into the silylenolether form which is then subjected to condensation with an aldehyde or an equivalent in the presence of a Lewis acid [e.g. anhydrous zinc chloride, anhydrous aluminum chloride ($AlCl_3$), anhydrous ferric chloride, titanium tetrachloride ($TiCl_4$), tin tetrachloride ($SnCl_4$), antimony pentachloride, cobalt chloride, cupric chloride, boron trifluoride ethyl ether complex, etc.], or converting a ketone form into the enolate by treating the ketone form with a metal triflate e.g. dialkyl boron tin (II) triflate) in the presence of an amine (e.g. triethylamine, pyridine, α-, β- or γ-picoline, 2,6-lutidine, 4-dimethylaminopyridine, 4-(1-pyrrolidinyl)pyridine, dimethylaniline, diethylaniline) followed by subjecting the enolate to condensation with an aldehyde or an equivalent. The condensation is conducted in a suitable solvent at a temperature ranging from about −100° C. to the boiling point of the solvent, preferably ranging from −78° to 100° C., for 1 minute to 3 days. The solvents employable for the reaction include water, liquid ammonia, alcohols (e.g. methanol, ethanol, propanol, isopropanol, butyl alcohol, sec-butyl alcohol, tert-butyl alcohol, ethylene glycol, methoxyethanol, ethoxyethanol), ethers (e.g. dimethyl ether, diethyl ether, tetrahydrofuran, dioxane, monoglyme, diglyme), halogenated hydrocarbons (e.g. dichloromethane, chloroform, carbon tetrachloride), aliphatic hydrocarbons (e.g. pentane, hexane, heptane), aromatic hydrocarbons (e.g. benzene, toluene, xylene), dimethylformamide, dimethylsulfoxide, hexamethylphospholamide, sulfolane and the suitable mixtures thereof. In the condensation by Wittig reaction, the employable reagents include metal hydroxides such as sodium hydroxide, potassium hydroxide, lithium hydroxide and barium hydroxide, metal alkoxides such as sodium methoxide, sodium ethoxide and potassium tert-butoxide, metal amides such as sodium amide and lithium diisopropylamide, metal hydrides such as sodium hydride and potassium hydride, organic metal compounds such as phenyllithium and butyllithium, and amines such as triethylamine, pyridine, α-, β- or γ-picoline, 2,6-lutidine, 4-dimethylaminopyridine, 4-(1-pyrrolidinyl)pyridine, dimethylaniline and diethylaniline. The reaction is conducted in a suitable solvent at a temperature ranging from about −20° C. to the boiling point of the solvent used, preferably ranging from about 0° to 150° C., for 1 minute to 10 days. The solvents employable for the reaction include liquid ammonia, alcohols (e.g. methanol, ethanol, propanol, isopropanol, butyl alcohol, sec-butyl alcohol, tert-butyl alcohol, ethylene glycol, methoxyethanol, ethoxyethanol), ethers (e.g. dimethyl ether, diethyl ether, tetrahydrofuran, dioxane, monoglyme, diglyme), aliphatic hydrocarbons (e.g. pentane, hexane, heptane), aromatic hydrocarbons (e.g. benzene, toluene, xylene), dimethylformamide, dimethylsulfoxide, hexamethylphospholamide, sulfolane and the suitable mixtures thereof.

The condensation can be conducted by using a Reformatsky reaction. The reagents employable for the Reformatsky reaction include zinc, magnesium, aluminum, and tin, and the reaction is conducted in a suitable solvent at a temperature ranging from about −20° C. to the boiling point of the solvent used, preferably ranging from about 0° to 150° C., for 30 minutes to 3 days. The solvents employable for the reaction include ethers (e.g. dimethyl ether, diethyl ether, tetrahydrofuran, dioxane, monoglyme, diglyme), alipahtic hydrocarbons (e.g. pentane, hexane, heptane), aromatic hydrocarbons (e.g. benzene, toluene, xylene), and the suitable mixtures thereof.

tetrahydrofuran, dioxane, monoglyme, diglyme), aromatic hydrocarbons (e.g. benzene, toluene, xylene), pyridine, dimethylformamide and the suitable mixtures thereof. The amount of reduction reagent used is about 1 to 100 moles, preferably about 2 to 20 moles per of the reduced compound. And, conversion of the compound (IX:$R^1$ being hydrogen atom) into the compound (IX:$R^1$ being a lower alkyl group as defined above) can be carried out for example by the following processes.

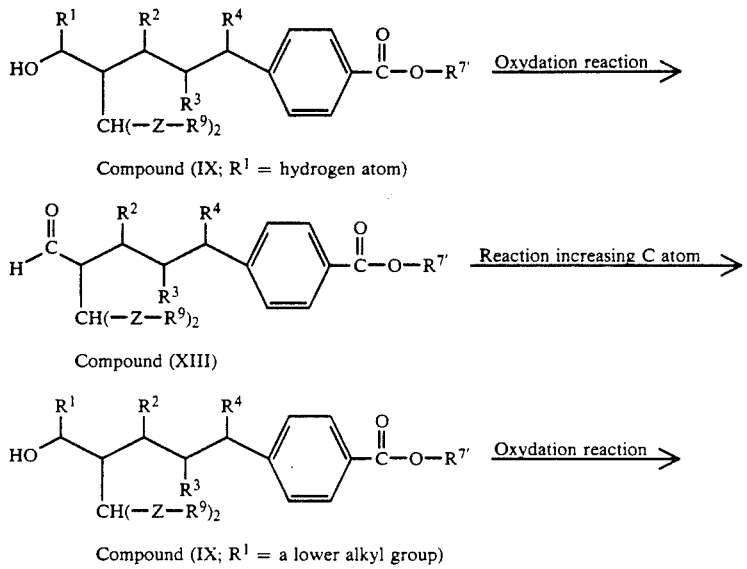

The reaction conditions for the catalytic reduction carried out continuously after the condensation are the same as those for the deesterification at the —$COOR^5$ and —$COOR^6$ of the compound (I) or a salt thereof (method C).

Process 2

This is the process whereby a group equivalent to aldehyde having a Cl unit is introduced into the active methylene (the α-position of the carboxylic acid ester) of the compound (VII). The group equivalent to aldehyde is exemplified by —CH(OCH$_3$)$_2$, —CH(OCH$_2$CH$_3$)$_2$, —CH(SCH$_3$)$_2$, —CH(OCH$_2$C$_6$H$_5$)$_2$, etc., and can be easily produced from the corresponding ortho-formic ester, ortho-thioformic ester, etc. by using known reagents according to the per se known method.

Process 3

The compound (VIII) obtained in the Process 2 is subjected to reduction by a hydride (e.g. lithium borohydride, sodium borohydride, lithium cyanoborohydride, lithium alminum hydride, di-isobutylalminum hydride) to give the alcohol form (IX:$R^1$ being hydrogen atom). In the reduction, $R^7$ and $R^8$ are desirably selected so as to create a difference of reactivity (or selectivity) against the carbonyl group of hydride between them.

The reduction is conducted in a suitable solvent at a temperature ranging from about −40° C. to the boiling point of the solvent used, preferably ranging from about 0° to 50° C. The solvent employable for the reaction include water, alcohols (e.g. methanol, ethanol, propanol, isopropanol, butyl alcohol, sec-butyl alcohol, tert-butyl alcohol, ethylene glycol, methoxyethanol, ethoxyethanol), acetic acid esters (e.g. methyl acetate, ethyl acetate), ethers (e.g. dimethyl ether, diethyl ether, This is the process whereby the compound (IX:$R^1$ being hydrogen atom) is oxidized to obtain the aldehyde form (XIII) and then the obtained form (XIII) is subjected to a reaction increasing carbon atoms to give the corresponding compound (IX:$R^1$ being a lower alkyl group). The oxidation reaction to obtain an aldehyde form can be carried out by using known reagents according to a per se known method. The reaction increasing carbon atom can be advantageously carried out by using organic metal reagents (e.g. Grignard reagent, alkyl lithium reagent, alkyl zinc reagent, etc.), and also can be carried out under known conditions according to a per se known method.

Process 4

The hydroxyl group of the alcohol form (IX) obtained in the Process 3 can be easily converted into the expected eliminatable group by a per se known method of halogenation, acylation or sulfonylation reaction.

Process 5

The compound (X) obtained in the Process 4 is subjected to condensation with malononitrile or a cyanoacetic acid ester represented by the formula NC—CH$_2$COOR$^{10}$ wherein R$^{10}$ is the same as described above, under a basic condition, to give the compound (XI). The employable bases, solvents and reaction conditions are in accordance with the known methods.

Process 6

The compound (XI), when treated with quanidine, can react at the cyano group or the ester residue followed by ring closure to form newly a pyrrolopyrimidine ring. Ring closure under a basic condition may allow the reaction to proceed advantageously. The employable bases include metal alkoxides such as sodium methoxide, sodium ethoxide, and potassium tert-butoxide. The employable solvents for the reaction include methanol, ethanol, propanol, tert-butyl alcohol, tetrahydrofuran, dioxane, dimethylsulfoxide and hexamethylphospholamide. The reaction temperature ranges from about 0° to 150° C., preferably from about 20° to 100° C. The reaction time ranges from about 1 to 24 hours.

Process 7

When the compound (XII) obtained in the Process 6 is subjected to deesterification of the ester residue [—COOR$^7$] and then to elimination of a protective group [ZR$^9$] in the protected group equivalent to aldehyde [—CH(ZR$^9$)$_2$], usually, the carboxylic acid (II-1) which is automatically oxidized in part can be obtained. For the deesterification are applicable the conditions used in the deesterification of the ester residues [—COOR$^5$ and —COOR$^6$] of the compound (I) (the methods A, B-1, B-2 and C). The elimination of a protective group [ZR9]in the group equivalent to aldehyde can be carried out according to a per se known method. The esterification and elimination of a protective group in the group equivalent to aldehyde may be conducted in any order.

Process 8

The compound (II-1) obtained in the Process 7 can be subjected to catalytic reduction under hydrogen atmosphere to obtain the tetrahydro form (II-2). As the conditions for the catalytic reduction are advantageously applicable those used in the deesterification of —COOR$^5$ and —COOR$^6$ of the compound (I) (the method C).

Though the compound (I-2) having a tetrahydropyridine ring as the ring (A) in the above formula (I) can be produced by subjecting the compound (II-2) and compound (III) to condensation, it is better to produce it by subjecting the compound (I-1) having a pyridine ring as the ring (A) in the formula (I) to catalytic reduction under hydrogen atmosphere. As the conditions for the catalytic reduction are applicable those used in the deesterification of —COOR$^5$ and —COOR$^6$ of the compound (I) or a salt thereof (the method C).

And, the compound (II) wherein the ring (A) is a benzene ring which may be hydrogenated, or a salt thereof can be produced for example by the following processes.

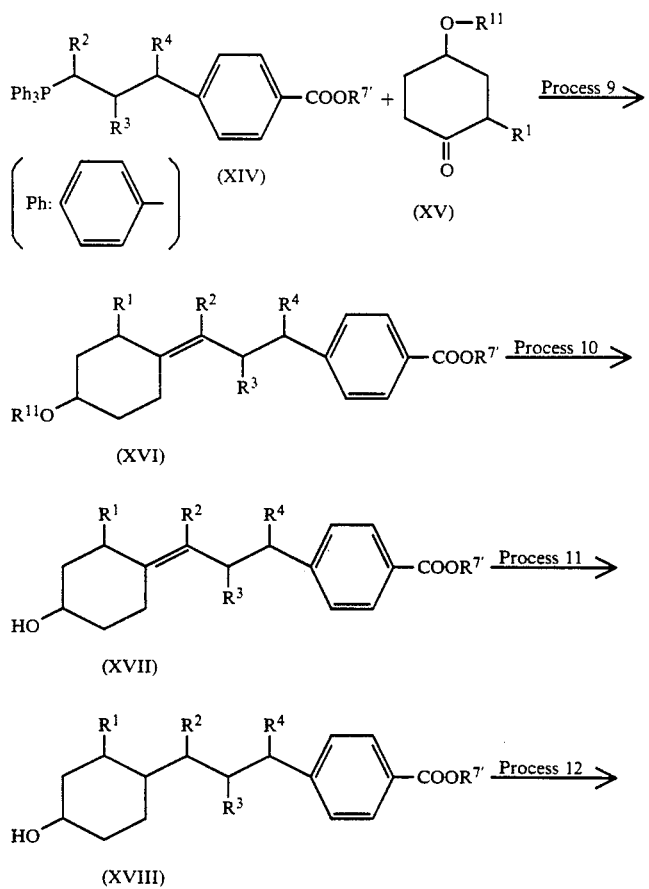

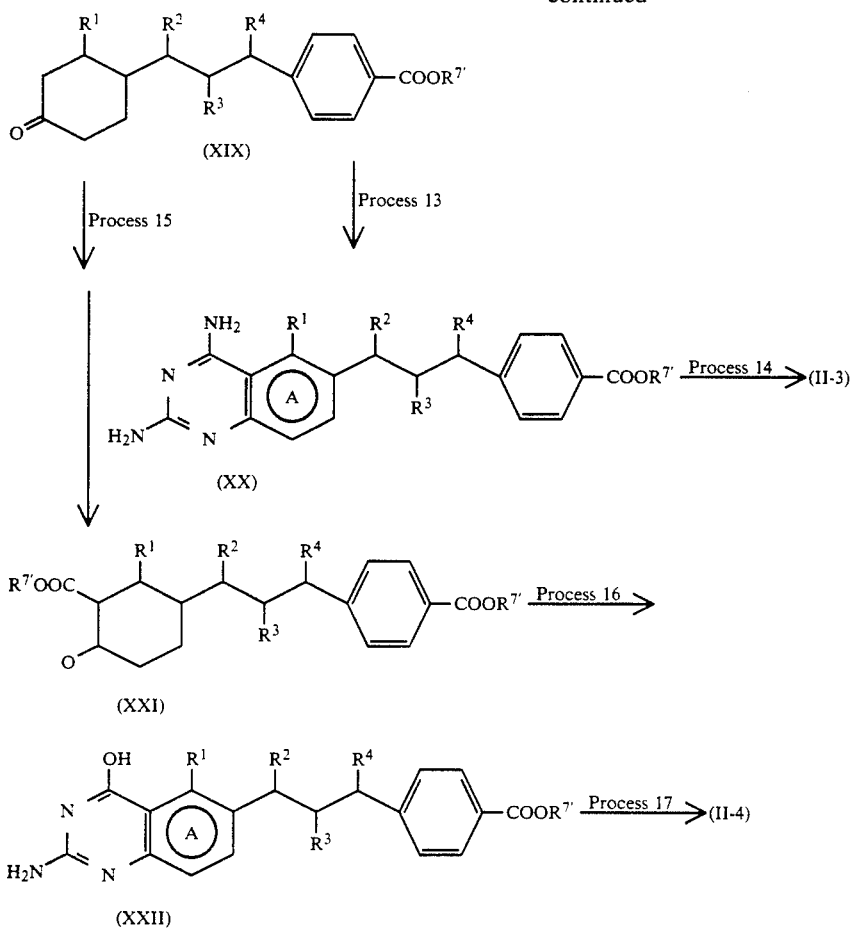

In the reaction formulas described above, $R^1$, $R^2$, $R^3$, $R^4$ and $R^7$ are the same as described before, and $R^{11}$ is a protecting group for a hydroxyl group. Such protecting groups of $R^{11}$ include for example $C_{1-6}$ alkyl groups (e.g., methyl, ethyl, n-propyl isopropyl, n-butyl, sec-butyl, tert-butyl, etc.), benzyl groups which may be substituted for example with one or two groups selected from nitro, $C_{1-3}$ alkoxy such as methoxy and ethoxy, halogen such as chlorine and bromine, cyano and phenyl (e.g., benzyl, p-nitrobenzyl, p-methoxybenzyl, p-chlorobenzyl, p-cyanobenzyl, diphenylmethyl, trityl, etc.), silyl groups which are substituted for example with the same or different three groups selected from $C_{1-6}$ alkyl as mentioned before, phenyl, triphenylmethyl, benzyl and xylyl (e.g. trimethylsilyl, triethylsilyl, isopropyldimethylsilyl, tert-butyldimethylsilyl, triphenylmethyldimethylsilyl, tert-butyldiphenylsilyl, methyldi-iso-propylsilyl, methyldi-tert-butylsilyl, tribenzylsilyl, trixylylsilyl, tri-iso-propylsilyl, triphenylsilyl, etc.), methoxymethyl group, isopropyloxymethyl group, tetrahydropiranyl group and tetrahydrofuranyl group. And, the esterified carboxyl group represented by —COOR$^{7'}$ is exemplified by such esterified carboxyl group as in "the carboxyl group which may be esterified" represented by —COOR$^7$.

The compounds (XX) and (XXII) may include acid addition salts as mentioned hereinafter in salts of the compound (I).

In the following, the reaction processes described before are explained in detail.

Process 9

The compound (XIV) prepared by known methods and the compound (XV) prepared by known methods are subjected to a Wittig reaction and condensed to obtain the compound (XVI). For the reaction conditions in this Wittig reaction are applicable those used in the Process 1.

Process 10

The protecting group $R^{11}$ for hydroxyl group in the compound (XVI) can easily be removed by using known reagents according to a per se known method, e.g., as described in "Protective Groups in Organic Chemistry", Plenum Press, London and New York (1973).

Process 11

The compound (XVII) obtained in the Process 10 can be subjected to reduction easily to give the compound (XVIII). The reduction can advantageously be carried out by catalytic reduction with addition of catalyst (e.g., nickel, palladium, platinum, rhodium, etc.) under an atmosphere of hydrogen. For the reaction conditions in the catalytic reduction are advantageously applicable those used in the deesterification of —COOR$^5$ and —COOR$^6$ of the compound (I) (the method C). The processes 10 and 11 may be conducted in any order to obtain the object compound of each process and finally to give the compound (XVIII).

Process 12

The compound (XVIII) obtained in the Process 11 can easily be converted to the ketone form (XIX) by using known reagents according to the per se known method.

Process 13

The compound (XIX) can be reacted with dicyanodiamide under heating followed by ring closure for forming newly a fused pyrimidine ring to obtain the compound (XX). The reaction temperature in this reaction ranges from 100° to 300° C., preferably from 150° to 250° C. And, the reaction time ranges from 1 to 24 hours. If necessary, the ring (A) can be converted into the corresponding aromatic ring by dehydrogenation with use of known reagents according to a per se known method.

Process 14

The ester form (XX) obtained in the Process 13 can be subjected to deesterification to obtain the carboxylic acid (II-3). The deesterification can be carried out according to the method used in the Process 7.

Process 15

The compound (XIX) obtained in the Process 12 can be activated in the α-position of the oxo group and then an ethoxycarbonyl group introduced thereto according to the conventional method to obtain the compound (XXI).

Process 16

The compound (XXI), when treated with guanidine, can react at the oxo group and ester residue followed by ring closure (i.e. cyclization) to form newly a fused pyrimidine ring. For the reaction conditions are applicable those used in the Process 6. And, if necessary, the ring (A) can be converted into the corresponding aromatic ring by dehydrogenation with use of known reagents according to a per se known method.

Process 17

The ester form (XXII) obtained in the Process 16 can be subjected to deesterification to obtain the carboxylic acid (II-4). The esterification can be carried out according to the method used in the Process 7.

The reactions, reagents and reaction conditions used in the Processes 1 to 17, and in the production of the starting compound (II) are known and explained in detail in the following literature. [J. F. W. Mcomine, Protective Groups in Organic Chemistry, Plenum Press, London and New York (1973)], [Pine, Hendrikson, Hammond, Organic Chemistry (4th edition)[I]-[II], Hirokawa Shoten (1982)], and [M. Fieser and L. Fieser, Reagents for Organic Synthesis vol. 1-10, Wiley-Interscience, New York, London, Sydney and Toronto (1969-1982)].

The compounds of this invention and intermediates thereof produced by these processes can be isolated from the reaction mixtures by the conventional means for separation and purification, such as concentration, extraction with solvent, chromatography, azeotrophy and recrystallization.

The compounds (I), (II) and (III) of this invention may form salts. Such salts are produced by the known methods, and exemplified by the salts of pharmaceutically acceptable bases or acids and quaternary salts. Salts of bases include salts of alkali metals, alkali earth metals, non-toxic metals, ammonium and substituted ammonium, such as sodium, potassium, lithium, calcium, magnesium, aluminum, zinc, ammonium, trimethylammonium, triethylammonium, triethanolammonium, pyridinium and substituted pyridinium. Salts of acids include salts of mineral acids such as hydrochloric acid, sulfuric acid, nitric acid, phosphoric acid and boric acid, and salts of organic acids such as oxalic acid, tartaric acid, acetic acid, trifluoroacetic acid, methanesulfonic acid and camphorsulfonic acid. Quaternary salts include salts of methyl bromide, methyl iodide, methyl methanesulfonate, methyl benzensulfonate and methyl p-toluenesulfonate.

Also, the compounds (I), (II) and (IV) may form zwitterions.

The compounds (I) or salts thereof of this invention exert excellent anti-tumor effects in mouse tumor cell strains (P388, L1210, L5178Y, B16 melanoma, MethA, Lewis Lung Carcinoma, S180 sarcoma, Ehrlich Carcinoma, Colon38) and human tumor cell strains (HL60, Lu65), decrease the tumors carried by warm-blooded animals [e.g. melanoma, sarcoma, mastocytoma, carcinoma, neoplasia, etc.], and prolong the life-span of tumor-carrying warm-blooded animals.

In the following are described the results indicating the pharmaceutical effects of the compounds (I) or salts thereof of this invention.

The cell growth inhibiting effect ($IC_{50}$) of the compounds obtained in the Working Examples 11 and 12 described below in HL-60 and HEL was determined by the following method. (1) A suspension of human leukemia cells ($2 \times 10^5$ cells/ml) in GTT culture medium (Wako Pure Chemicals) including the compound of this invention was inoculated into each well of the 96-microwell plate (0.2 ml in a well), and subjected to standing culture at 37° C. under 5% $CO_2$ for 68 hours. To this was added $1\mu Ci$-[$^3H$]thymidine (5Ci/mmol) and subjected again to culture for 4 hours. In order to measure the thymidine taken up in the cells, fractions insoluble in acid were collected and radioactivity thereof was measured by liquid scinthillation counter. The $IC_{50}$ value of a compound was defined as the concentration of the compound required to decrease the radioactivity taken up in the untreated control group by 50%. (2) A suspension of human embryonic lung fibroblast HEL ($1 \times 10^4$ cells/ml) in MEM culture medium (Japan Flow Laboratories) were inoculated into each well of the 96-microwell plate (0.1 ml in a well), and subjected to standing culture at 37° C. under 5% $CO_2$ for 24 hours. To this was added MEM culture medium including the compound of this invention, and subjected again to culture for 72 hours. Then the culture was substituted with a culture medium including MTT (Dojindo Laboratories) in 1 μg, and thereto was added 10% SDS (Wako Pure Chemicals), followed by incubating for one night. The absorbance at 590 nm was measured by multiscan (Titertek) and the $IC_{50}$ value was defined in comparison with the untreated control group. The results obtained are shown in Table 1.

TABLE 1

| Test compound | HL-60 (μg/ml) | HEL (μg/ml) |
|---|---|---|
| Compound of Working Example 11 | <0.0025 | 10.0 |
| Compound of Working Example 12 | <0.0025 | 5.0 |

As shown by the above-mentioned results, the compounds (I) and salts thereof are excellent in inhibition of cell growth of HL-60, while they do not exert a toxicity against HEL. The compounds (I) of this invention and salts thereof are of low toxicity, having remarkable antitumor effects. Therefore, the preparations containing the compound (I) or salt thereof can be employed as anti-tumor agents for the treatment of tumors in warm-blooded animals, particularly mammals (e.g. human, mouse, rat, cat, dog, rabbit, etc.).

The compounds (I) and salts thereof, when used as anti-tumor agents, can be administered orally and parenterally as they are and in the forms of powders, granules, tablets, capsules, suppositories and injections, which are prepared according to the conventional methods using pharmaceutically acceptable excipients, vehicles and diluents. The dose varies according to the animals, diseases, symptoms, compounds and administration routes; for example, the daily dose is about 1.0 to 50 mg of the compound of this invention per kg of body weight of a warm-blooded animal described above for oral administration, and about 1.0 to 20 mg/kg for parenteral administration. Injections may be administered intramuscularly, intraperitoneally, subcutaneously or intravenously.

The preparations are produced by a per se known processes. The above-mentioned oral preparations, for example tablets, are produced by suitable combination with a binder (e.g. hydroxypropylcellulose, hydroxypropylmethylcellulose, macrogol, etc.), a disintegrator (e.g. starch, calcium carboxylmethylcellulose, etc.), or a lubricant (e.g. magnesium stearate, talc, etc.).

The parenteral preparations, for example injections, are produced by suitable combination with an isotonicity producing agent (e.g. glucose, D-sorbitol, D-mannitol, sodium chloride, etc.), an antiseptic (e.g. benzyl alcohol, chlorobutanol, methyl p-hydroxybenzoate, propyl p-hydroxybenzoate, etc.), or a buffer (e.g. phosphate buffer, sodium acetate buffer, etc.).

An example of a process for production of tablets comprises mixing about 1.0 to 50 mg of the compound of this invention, 100 to 500 mg of lactose, about 50 to 100 mg of corn starch and about 5 to 20 mg of hydroxypropylcellulose for preparation of a tablet by a conventional means, granulating, mixing with corn starch and magnesium stearate and tabletting, so that tablets each weighing about 100 to 500 mg with the diameter of about 3 to 10 mm are obtained. The tablets may be coated with a mixture of acetone and ethanol, the mixture containing hydroxypropylmethylmethylcellulose phtalate (about 10 to 20 mg per tablet) and castor oil (0.5 to 2 mg) at a concentration of about 5 to 10%, to give enteric coated tablets.

An example of a process for preparation of an injection comprises dissolving about 5.0 to 50 mg of the sodium salt of the compound of this invention in about 2 ml of physiological saline for preparation of an ampoule, sealing the resultant solution in an ampoule and sterilizing the ampoule at 110° C. for about 30 minutes, or dissolving about 5.0 to 50 mg of the sodium salt of the compound of this invention in about 2 ml of sterile distilled water wherein about 10 to 40 mg of mannitol or sorbitol is dissolved into the ampoule, freeze-drying and sealing the ampoule. For use of the freeze-dried compound for subcutaneous, intravenous or intramuscular injection, the ampoule is opened and the content is dissolved in, for example, physiological saline so that the concentration of the compound may be about 1.0 to 20 mg/ml.

The following Reference Examples and Working Examples will explain the present invention in more concrete. But, the present invention should not be limited by these Examples. In these examples, room temperature means about 20° C.

REFERENCE EXAMPLE 1

Production of methyl 5-[4-(tert-butoxycarbonyl)phenyl]pentanoate

Under an atmosphere of argon, potassium (25 g) was added to dried tert-butyl alcohol (820 ml), which was refluxed by heating to be dissolved completely. The solution was cooled to 20° C. to which ether (300 ml) was added and then a solution of methyl crotonate (63.93 g) and tert-butyl 4-formylbenzoate (71.0 g) in tert-butyl alcohol-ether (2:1, 300 ml) was added slowly while the inner temperature was kept at 10° C. After stirring at the same temperature for 2 hours, 1N potassium hydrogen sulfate in water (75 ml) was added with cooling so that the pH might be adjusted to 4. The solution was extracted with ether, washed with water and then with saturated saline, and subjected to evaporation of the solvent under reduced pressure. The resultant residue was dissolved in ethyl acetate (100 ml), to which 5%Pd-C (15 g: Engelhard Co.) was added and stirred vigorously under hydrogen pressure of 4 kg/cm$^2$ at room temperature for 3 hours. The catalyst was filtrated off, the solvent was evaporated under reduced pressure, to the residue were added dried methanol (200 ml), 4-(N,N-dimethylamino)pyridine (30 mg) and dichloromethane (250 ml), and then a solution of 1,3-dicyclohexylcarbodiimide (132 g) in dichloromethane (250 ml) was slowly added dropwise at 0° C. After stirring at room temperature for 18 hours, the mixture was cooled to 0° C., and acetic acid (30 ml) was added and stirred at 0° C. for 30 minutes and then at room temperature for 30 minutes. The resultant precipitate was filtrated off, the filtrate was concentrated to dryness under reduced pressure, to the residue was added ethyl acetate (100 ml) and kept at 0° C. for 2 hours, and the resultant precipitate was again filtrated off. The filtrate was concentrated under reduced pressure and the residue was purified by column chromatography (support; silica gel, 500 g, developing agent; ether:hexane=1:15→1:5), to give the object compound (59.7 g).

Melting point (Bp) 145°-155° C./0.2-0.3 mmHg
IR (Neat) : 2980, 2950, 1740, 1712, 1605 cm$^{-1}$
$^1$H-NMR (CDCl$_3$) δ: 1.40-1.75 (4H,m), 1.55 (9H,s), 2.15-2.45 (2H,m), 2.50-2.75 (2H,m), 3.62 (3H,s), 7.16 (2H,d,j=8 Hz), 7.85 (H,d,j=8 Hz).

REFERENCE EXAMPLE 2

Production of methyl 5-[4-(tert-butoxycarbonyl)phenyl]-2-(dimethoxymethyl)pentanoate Under an atmosphere of argon, to a solution of diisopropylamine (8.35 g) in tetrahydrofuran (150 ml) was added a solution of butyllithium (82.5 mmol) in hexane (51.6 ml) at 0° C. and stirred for 10 minutes, to which, after cooling to −78° C., a solution of the compound (21.93 g) obtained in the Reference Example 1 in tetrahydrofuran (50 ml) was added dropwise over 30 minutes. After stirring for 30 minutes, chlorotrimethylsillane (15 ml) was added in one portion. The temperature of the mixture was brought up to room temperature over 2 hours, followed by evaporation of the solvent and addition of dried toluene (30 ml×2). Chloro-trimethylsilane was completely evaporated off under reduced pressure. To the residue was added dried toluene (30 ml). After the insoluble matter was removed by filtration, the solvent was evaporated under reduced pressure to obtain ketene silyl acetal of the intermediate. Under an atmosphere of argon, tin (I) chloride (2.84 g) and triphenylmethyl chloride (4.18 g) were suspended in dichloromethane (150 ml), and thereto was slowly added a solution of ketene silyl acetal described above and methyl orthoformate (9.55 g) in dichloromethane (50 ml). When the clear yellow color of the reaction mixture disappeared, titanium tetrachloride (1.5 ml) was added thereto. After stirring at −78° C. for 30 minutes, the reaction mixture was added to a solution (150 ml) of 0.5N sodium hydrogen carbonate, followed by stirring at room temperature for 30 minutes. The precipitate was removed by filtration and the filtrate was extracted by dichloromethane. The extract was dried over anhydrous sodium sulfate and the solvent was evaporated under reduced pressure. The obtained residue was purified by column chromatography (support; silica gel, 200 g, developing agent; ethyl acetate:hexane=1:12.1:8) to give the object compound (11.0 g).

IR (Neat) : 2940, 1740, 1715, 1608 cm$^{-1}$ $^1$H-NMR (CDCl$_3$) δ: 1.40–1.85 (4H,m), 1.57 (9H,s), 2.45–2.90 (3H,m), 3.30 (3H,s), 3.33 (3H,s), 3.69 (3H,s), 4.48 ($^1$H,d,j=8Hz), 7.20 (2H,d,j=8Hz), 7.88 (2H,d,j=8Hz).

REFERENCE EXAMPLE 3

Production of t-butyl 4-[4-(dimethoxymethyl)-5hydroxypentyl]benzoate

Under an atmosphere of argon, to a solution of the compound (11.0 g) obtained in the Reference Example 2 in ether (50 ml) was added lithium boron hydride (980 mg) at 0° C., and the temperature was quickly brought up to room temperature, followed by stirring over night. To the reaction mixture was added methanol (70 ml) at 0° C., and after stirring for 30 minutes, the pH was adjusted to 6 with ice-water (10 ml) and 1N potassium hydrogen sulfate aqueous solution. The mixture was extracted with ether, and the extract was washed with water, then with saturated sodium chloride solution and dried over anhydrous sodium sulfate. The solvent was evaporated under reduced pressure and the residue was purified by column chromatography (support; silica gel, 200 g, developing agent; ethyl acetate: hexane=1:3) to obtain the object compound (7.98 g).

IR (Neat) : 3450, 2925, 1707, 1604 cm$^{-1}$ $^1$H-NMR (CDCl$_3$) δ: 1.20–1.95 (5H,m), 1.60 (9H,s), 2.33 (2H,t,J=8 Hz), 2.40 (1H,brs), 3.35 (3H,s), 3.41 (3H,s), 3.50–3.73 (2H,m), 4.27 (1H,d,J=6 Hz), 7.21 (2H,d,J=8 Hz), 7.90 (2H,d,J=8 Hz).

REFERENCE EXAMPLE 4

Production of imethoxymethyl)-5(methylsulfonyloxy)pentyl]benzoate

The compound (7.98 g) obtained in the Reference Example 3 was dissolved in a mixture of pyridine and dichloromethane (1:1, 40 ml) and thereto was added methanesulfonyl chloride (3.24 g) at −15° C. The temperature was quickly brought up to 0° C., followed by stirring for 2 hours. The solvent was evaporated under reduced pressure and to the residue were added ether (150 ml) and triethylamine (476 mg), followed by stirring for 3 minutes. The ether layer was washed with water, a saturated aqueous copper sulfate solution and a saturated sodium chloride solution in this order, and then dried over anhydrous sodium sulfate. The solvent was evaporated under reduced pressure to obtain the object compound (9.83 g).

IR (Neat): 2940, 1714, 1608, 1370, 1180 cm$^{-1}$ $^1$H-NMR (CDCl$_3$) : 1.30–1.80 (5H,m), 1.63 (9H,s), 2.68 (2H,t,J=7 Hz), 3.00 (3H,s), 3.43 (6H,s), 4.20–4.35 (3H,m), 7.26 (2H,d,J=8 Hz), 7.93 (2H,d,J=8 Hz).

REFERENCE EXAMPLE 5

Production of ethyl 7-[4-tert-butoxycarbonyl)phenyl]-2-cyano-4-(dimethoxymethyl)heptanoate Under an atmosphere of argon, to a suspension of potassium tert butoxide (10.60 g) and sodium iodide (3.54 g) in tetrahydrofuran (100 ml) was added dropwise a solution of ethyl cyanoacetate (10.68 g) in tetrahydrofuran (50 ml) and hexamethylphosphoramide (25 ml) at 0° C. After stirring at room temperature for 5 minutes, to this mixture was added a solution of the compound (9.83 g) obtained in the Reference Example 4 in tetrahydrofuran (50 ml). After reflux by heating for 2.5 hours, the temperature was cooled down to room temperature. The reaction mixture was poured into ice water and adjusted to pH 6 with 1N potassium hydrogen sulfate aqueous solution. Extraction was conducted with ether, and the extract was washed with water and then saturated sodium chloride solution and dried over anhydrous sodium sulfate. The solvent was evaporated under reduced pressure and the resulting residue was purified by column chromatography (support; silica gel, 250 g, developing agent; ethyl acetate: hexane=1:7) to obtain the object compound (7.52 g).

IR (Neat): 2980, 2940, 2245, 1748, 1713, 1697 cm$^{-1}$ $^1$H-NMR (CDCl$_3$) δ: 1.20–2.20 (7H,m), 1.30 (3H,d,J=7Hz), 1.60 (9H,s), 2.66 (2H,t,J=7Hz), 3.30–3.40 (6H,m), 3.63–4.10 (1H,m), 4.15 (1H,d,J=3Hz), 4.23 (2H,t,J=7Hz), 7.23 (2H,d,J=8Hz), 7.93 (2H,d,J=8Hz).

REFERENCE EXAMPLE 6

Production of tert-butyl 4-[5-(2,6-diamino-4-hydroxypyrimidin-5-yl)-4-(dimethoxymethyl)pentyl]benzoate To a solution of potassium tert-butoxide (3.89 g) and guanidine hydrochloride (1.99 g) in tert-butyl alcohol (30 ml) was added a solution of the compound (7.52 g) obtained in the Reference Example 5 in tert-butyl alcohol (30 ml) under an atmosphere of argon, and refluxed by heating for 3.5 hours. To the reaction mixture were added acetic acid (834 mg) and water (50 ml), followed by extraction with a chloroform-tetrahydrofuran mixture (1:1). The solvent was evaporated under reduced pressure and the resulting residue was purified by column chromatography (support; silica gel, 240 g, developing agent; dichloromethane: ethanol=10:1) to obtain the object compound (5.14 g).

IR (KBr): 3350, 2930, 1710, 1620, 1497, 1450 cm$^{-1}$ $^1$H-NMR (CDCl$_3$) δ: 1.10–2.00 (5H,m), 1.56 (9H,s), 2.10–2.40 (2H,m), 2.58 (2H,brt,J=7 Hz), 3.33 (3H,s), 3.38 (3H,s), 4.12 (1H,d,J=4 Hz), 5.03 (2H,brs), 5.70 (2H,brs), 7.18 (2H,d,J=8 Hz), 7.78 (2H,d,J=8 Hz).

REFERENCE EXAMPLE 7

Production of tert-butyl 4-[6,6-dicyano-4-dimethoxymethyl)hexyl]benzoate

Under an atmosphere of argon, to a suspension of sodium hydride (3.00 g) and sodium iodide (3.75 g) in dimethylsulfoxide (15 ml) was added dropwise a solution of malononitrile (8.26 g) in dimethylsulfoxide (15 ml) under ice cooling. After stirring at room temperature for 15 minutes, a solution of the compound (10.41 g) obtained in the Reference Example 4 in dimethylsulfoxide (15 ml) was added, followed by heating at 60° C. for 5 hours and then cooling to room temperature. The reaction mixture was poured into ice water and adjusted to pH 6 with 1N potassium hydrogen sulfate aqueous solution. The organic layer extracted with ether was washed with water and saturated sodium chloride solution in this order, and then dried over anhydrous sodium sulfate. The solvent was evaporated under reduced pressure and the resulting residue was purified by column chromatography (support; silica gel, 300 g, developing agent; ethyl acetate: hexane = 1:8) to obtain the object compound (6.97 g).

IR (Neat): 2948, 2255, 1715, 1605 cm$^{-1}$
$^1$H-NMR (CDCl$_3$) : 1.15–2.50 (7H,m), 1.60 (9H,s), 2.67 (2H,t,J=7 Hz), 3.36 (3H,s), 3.40 (3H,s), 4.13 (1H,d,J=3 Hz), 4.32 (1H,dd,J=10 Hz,6 Hz), 7.20 (2H,d,J=8 Hz), 7.90 (2H,d,J=8 Hz).

REFERENCE EXAMPLE 8

Production of tert-butyl 4-[5-(2,4,6-triaminopyridin-5-yl)-4-(dimethoxymethyl)-pentyl]benzoate The compound (663 mg) obtained in the Reference Example 7 was subjected to the same reaction as that in the Reference Example 6, to obtain the object compound (648 mg).

IR (KBR): 3480, 3390, 3200, 2940, 1710, 1604, 1570, 1430 cm$^{-1}$
$^1$H-NMR (CDCl$_3$) δ: 1.30–2.00 (5H,m), 1.60 (9H,s), 2.05–2.43 (2H,m), 2.43–2.77 (2H,m), 3.34 (3H,s), 3.39 (3H,s), 4.15 (1H,d,J=3 Hz), 4.47 (2H,brs), 4.62 (4H,brs), 7.18 (2H,d,J=8 Hz), 7.88 (2H,d,J=8 Hz).

REFERENCE EXAMPLE 9

Production of tert-butyl 4-[4-(dimethoxymethyl)-5-oxopentyl]benzoate

To a solution of oxalyl chloride (558 mg) in dichloromethane (10 ml) was added a solution of dimethyl sulfoxide (668 mg) in dichloromethane (2 ml) at −50° C., followed by stirring for 2 minutes, and to the resulting reaction mixture was added a solution of the compound (1.354 g) obtained in the Reference Example 3 in dichloromethane (5 ml) and thereto after stirring for 15 minutes was added dropwise triethylamine (2.8 ml). After stirring for 5 minutes, the temperature was brought up to room temperature over 30 minutes. To the resulting mixture was added water (20 ml), followed by extraction with dichloromethane. The extract was dried over anhydrous sodium sulfate. The solvent was evaporated under reduced pressure and the resulting residue was purified by column chromatography (support; silica gel, 20 g, developing agent; ethyl acetate; hexane = 1:5), to obtain the object compound (1.27 g).

IR (KBr): 2975, 2940, 1727, 1708, 1604 cm$^{-1}$
$^1$H-NMR (CDCl$_3$) δ: 1.40–1.80 (4H,m), 1.55 (9H,s), 2.45–2.76 (3H,m), 3.30 (3H,s), 3.33 (3H,s), 4.45 (1H,d,J=6Hz), 7.15 (2H,d,J=8 Hz), 7.85 (2H,d,J=8 Hz), 9.60 (1H,d,J=4 Hz).

REFERENCE EXAMPLE 10

Production of tert-butyl 4-[4-(dimethoxymethyl)-5-hydroxyhexyl]benzoate

To a solution of the compound (5.45 g) obtained in the Reference Example 9 in tetrahydrofuran (15 ml) was added dropwise a solution of methyl magnesium bromide in tetrahydrofuran (12.3 ml, 24.1 mmol) at −78° C. under an atmosphere of argon. After stirring at −78° C. for 1 hour and then at room temperature for 1 minute, a saturated aqueous ammonium chloride solution (80 ml) was added, followed by extraction with ether. The obtained organic layer was washed with saturated sodium chloride solution and dried over anhydrous sodium sulfate. The solvent was evaporated under reduced pressure and the resulting residue was purified by column chromatography (support; silica gel, 100 g, developing agent: ethylacetate: hexane = 1:3), to obtain the object compound (4.46 g).

IR (Neat): 3480, 2980, 2940, 1712, 1608 cm$^{-1}$
$^1$H-NMR (CDCl$_3$) δ: 1.07 (1.5H,d,J=7 Hz), 1.12 (1.5H,d,J=7 Hz), 1.25–1.90 (5H,m), 1.54 (9H,s), 2.50–2.75 (2H,m), 3.93 (1H,d,J=5 Hz), 3.30 (1.5H,s), 3.32 (1.5H,s), 3.37 (3H,s), 3.70–4.20 (1H,m), 4.27 (0.5H,d,J=7 Hz), 4.32 (0.5H,d,J=5 Hz), 7.18 (2H,d,J=8 Hz), 7.84 (2H,d,J=8 Hz).

REFERENCE EXAMPLE 11

Production of tert-butyl 4-[4-(dimethoxymethyl)-5-(methylsulfonyloxy)hexyl]-benzoate The compound (4.46 g) obtained in the Reference Example 10 was subjected to the same reaction as that in the Reference Example 4, to obtain the object compound (5.45 g).

IR (Neat): 2920, 1700, 1604, 1340, 1170 cm$^{-1}$
$^1$H-NMR (CDCl$_3$) δ: 1.20–1.95 (5U,s), 1.33 (1.5H,d,J=6 Hz), 1.40 (1.5H,d,J=5 Hz), 1.59 (9H,s), 2.66 (2H,t,J=7 Hz), 2.95 (3H,s), 3.35 (6H,s), 4.22 (1H,dd,J=8 Hz, 6 Hz), 4.83–5.13 (1H,m), 7.21 (2H,d,J=8 Hz), 7.89 (2H,d,J=8 Hz).

REFERENCE EXAMPLE 12

Production of ethyl 7-[4-(tert-butoxycarbonyl)phenyl]-2-cyano-3-methyl-4-(dimethoxymethyl)]heptanoate The compound (5.70 g) obtained in the Reference Example 11 was subjected to the same reaction as that in the Reference Example 5, to obtain the object compound (2.88 g).

IR (KBr): 2980, 2940, 2240, 1743, 1710, 1604 cm$^{-1}$
$^1$H-NMR (CDCl$_3$) δ: 0.88–1.15 (3H,m), 1.20–1.80 (6H,m), 1.31 (3H,t,J=7 Hz), 1.58 (9H,s), 2.65 (2H,t,J=7.5 Hz), 3.35 (6H,s), 4.07–4.25 (2H,m), 4.23 (2H,q,J=7 Hz), 7.20 (2H,d,J=8 Hz), 7.89 (2H,d,J=8 Hz).

REFERENCE EXAMPLE 13

Production of tert-butyl 4-[5-(2,6-diamino-4-hydroxypyrimidin-5-yl)-4-(dimethoxymethyl)-5-methylpentyl]benzoate The compound (569 mg) obtained in the Reference Example 12 was subjected to the same reaction as that in the Reference Example 6, to obtain the object compound (274 mg) as the diastereomers in proportion of 1:3 (according to the elution).

Main-product:

IR (KBr): 3350, 2978, 2940, 1710, 1650, 1640-1600 cm$^{-1}$ $^1$H-NMR (CDCl$_3$) δ: 1.25 (3H,d,J=7 Hz), 1.30-1.95 (4H,m), 1.60 (9H,s), 2.03-2.33 (1H,m), 2.40-2.73 (3H,m), 3.26 (3H,s), 3.31 (3H,s), 4.05 (1H,d,J=3 Hz), 4.83 (2H,brs), 5.38 (2H,brs), 7.21 (2H,d,J=8 Hz), 7.89 (2H,d,J=8 Hz).

By-product

IR (KBr): 3350, 2935, 1710, 1637, 1620, 1605 cm$^{-1}$ $^1$H-NMR (CDCl$_3$) δ: 1.25-1.85 (4H,m), 1.31 (3H,d,J=7 Hz), 1.60 (9H,s), 1.95-2.25 (1H,m), 2.55 (2H,t,J=7 Hz), 2.60-2.90 (1H,m), 3.38 (6H,s), 4.27 (2H,d,J=5 Hz), 4.93 (2H,brs), 5.25 (2H,brs), 7.17 (2H,d,J=8 Hz), 7.83 (2H,d,J=8 Hz).

REFERENCE EXAMPLE 14

Production of 5-[4-(tert-butoxycarbonyl)phenyl]-5-hydroxy-2-hexenoic acid

To a suspension obtained by adding a solution of 4-acetylbenzoic acid tert-butyl ester (7.82 g) in benzene-ether-tetrahydrofuran (3:3:2, 80 ml) to 4.64 g (71 mmol) of zinc, were added gradually under heating and stirring 4-bromocrotonic acid methyl ester (6.36 g) and iodine (20 mg). After reflux under heating in an oil bath at 70° C. for 1 hour, methyl 4-bromocrotonate (2.13 g) and zinc (1.55 g) were added, followed by reflux under heating for 30 minutes. The temperature was cooled down to room temperature, and the reaction mixture was poured into water (300 ml) and adjusted to pH 5 with acetic acid. The organic layer obtained by extraction with ether was washed with 5% aqueous ammonia and then dried over anhydrous magnesium sulfate. The solvent was evaporated under reduced pressure and the resulting residue was purified by column chromatography (support; silica gel, 200 g, developing agent; ethyl acetate:hexane=1:4), to obtain the object compound (9.2 g).

IR (Neat): 3480, 2975, 1720, 1700, 1650, 1605 cm$^{-1}$ $^1$H-NMR (CDCl$_3$) δ: 1.53 (12H,s), 2.64 (2H,d,j=7 Hz), 2.67 (1H,brs), 3.63 (3H,s), 5.80 (1H,d,j=15 Hz), 6.80 (1H,dt, j=15 Hz,7 Hz), 7.45 (2H,d,j=8 Hz), 7.90 (2H,d,j=8 Hz).

REFERENCE EXAMPLE 15

Production of methyl 5-[4-(tert-butoxycarbonyl)phenyl]hexanoate

To a solution of the compound (120 mg) obtained in the Reference Example 14 in ethanol (3 ml) were added 10% Pd-C (60 mg) and acetic acid (30 mg), followed by vigorous stirring for 10 hours under hydrogen pressure of 4 kg/cm$^2$. The catalyst was removed by filtration, and the solvent was evaporated under reduced pressure. The resulting residue was purified by column chromatogbraphy (support; silica gel, 10 g, developing agent; ethyl acetate:hexane=1), to obtain the object compound (107 mg) as a colorless oil.

IR (Neat): 2950, 2920, 1735, 1700, 1602 cm$^{-1}$ $^1$H-NMR (CDCl$_3$) : 1.20-1.75 (4H,m), 1.23 (3H,d, j=6.5 Hz), 1.57 (9H,s), 2.24 (2H,brt,j=6.5 Hz), 2 53-2.95 (1H,m), 3.62 (3H,s), 7.21 (2H,d,j=8 Hz), 7.90 (2H,d, j=8 Hz).

REFERENCE EXAMPLE 16

Production of 5-[4-(tert-butoxycarbonyl)phenyl]-2-(dimethoxymethyl)hexanoic acid The compound (5.62 g) obtained in the Reference Example 15 was subjected to the same reaction as that in the Reference Example 2, to obtain the object compound (4.86 g).

IR (Neat): 2959, 1732, 1703, 1600 cm$^{-1}$ $^1$H-NMR (CDCl$_3$) δ: 1.22 (3H,d, j=7 Hz), 1.25-1.70 (4H,m), 1.59 (9H,s), 2.50-2.90 (2H,m), 3.25 (3H,s), 3.31 (3H,s), 3.68 (3H,s),4.43 (1H,dd,j=8 Hz,3 Hz), 7.20 (2H,d, j=8 Hz), 7.93 (2H,d, j=8 Hz).

REFERENCE EXAMPLE 17

Production of tert-butyl 4-[4-(dimethoxymethyl)-5-hydroxy-1-methylpentyl]benzoate The compound (4.83 g) obtained in the Reference Example 16 was subjected to the same reaction as that in the Reference Example 3, to obtain the object compound (4.14 g).

IR (Neat): 3460, 2940, 1712, 1606, 1570 cm$^{-1}$ $^1$H-NMR (CDCl$_3$) δ: 1.10-2.20 (6H,m), 1.24 (3H,d, j=7 Hz), 1.56 (9H,s), 2.72 (1H,tq,j=7 Hz,7 Hz), 3.28 (3H,s), 3.36 (3H,s), 3.45-3.68 (2H,m), 4.20 (1H,d,j=6 Hz), 7.20 (2H,d,j=8 Hz), 7.88 (2H,d,j=8 Hz).

REFERENCE EXAMPLE 18

Production of tert-butyl 4-[4 (dimethoxymethyl)-1-methyl-5-(methylsulfonyloxy)-pentyl]benzoate The compound (4.13 g) obtained in the Reference Example 17 was subjected to the same reaction as that in the Reference Example 4, to obtain the object compound (5.03 g).

IR (Neat): 2970, 2945, 1713, 1608, 1360, 1175 cm$^{-1}$ $^1$H-NMR (CDCl$_3$) δ: 1.20-1.80 (4H,m), 1.25 (3H,d, j=7 Hz), 1.56 (9H,s), 2.72 (2H,tq,j=7 Hz,7 Hz), 2.91 (1.5H,s), 2.92 (1.5H,s), 3.30 (3H,s), 3.31 (1.5H,s), 3.32 (1.5H,s) 4.15-4.26 (3H,m), 7.21 (2H,d,j=8 Hz), 7.90 (2H,d,j=8 Hz).

REFERENCE EXAMPLE 19

Production of ethyl 7-[4-(tert-butoxycarbonyl)phenyl]-2-cyano-4-(dimethoxymethyl)octanoate The compound (5.25 g) obtained in the Reference Example 18 was subjected to the same reaction as that in the Reference Example 5, to obtain the object compound IR (Neat): 2960, 2930, 2240, 1745, 1710, 1603 cm$^{-1}$ $^1$H-NMR (CDCl$_3$) : 1.10 2.20 (7H,m), 1.25 (3H,d, j=7 Hz), 1.31 (3H,t,j=7 Hz), 1.58 (9H,s), 2.68 (1H,tq,j=7 Hz,7 Hz), 3.20-3.40 (6H,m), 4.00-4.10 (2H,m), 4.21 (2H, q,j=7 Hz), 7.20 (2H,d, j=8 Hz), 7.91 (2H,d,j=8 Hz).

REFERENCE EXAMPLE 20

Production of tert-butyl 4-[5-(2,6-diamino-4-hydroxypyridin-5-yl)-4-(dimethoxymethyl)-1-methylpentyl]benzoate The compound (3.84 g) obtained in the Reference Example 19 was subjected to the same reaction as that in the Reference Example 6, to obtain the object compound (3.64 g).

IR (KBr): 3355, 3220, 2965, 2940, 1713, 1620 cm$^{-1}$ $^1$H-NMR (CDCl$_3$) δ: 1.10–1.95 (5H,m), 1.19 (3H,d, j=7 Hz), 1.58 (9H,s), 2.15–2.40 (2H,m), 2.50–2.83 (1H,m), 3.20–3.40 (6H,m), 4.10 (1H,d,j=4.5 Hz), 5.00 (2H,brs), 5.62 (2H,brs), 7.20 (2H, d,j=8 Hz), 7.90 (2H,d,j=8 Hz).

REFERENCE EXAMPLE 21

Production of 4-[(tert-butyldimethylsilyl)oxy]cyclohexanol

To a solution of 1,4-cyclohexandiol (cis: trans=ca. 1:1, 25.0 g) and t-butylchlorodimethylsilane (32.4 g) in dimethylformamide (150 ml) was added slowly and dropwise a solution of triethylamine 21.8 g) and 4-(dimethylamino)pyridine (1.05 g) in dimethylformamide (50 ml) at 0° C. After stirring for one hour, to the reaction mixture were added water and ether. The ether layer was separated, washed with water and saturated aqueous sodium chloride and dried over anhydrous magnesium sulfate. The solvent was evaporated under reduced pressure and the resulting residue was purified by column chromatography (support; silica gel, 300 g, developing agent; ethyl acetate : hexane=1:5) to obtain the object compound (17.8 g) as a mixture of cis and trans isomers (ca. 1:1).

IR (Neat): 3350, 2955, 2940, 2895, 2865, 1375, 1255 cm$^{-1}$ $^1$H-NMR (CDCl$_3$) δ: −0.03 (6H,s), 0.90(9H,s), 1.13–1.90 (8H,m), 1.30(1H,s , 3,40–3.80 (2H,m) cm$^{-1}$.

REFERENCE EXAMPLE 22

Production of t-[(tert butyldimethylsilyl)oxy]-cyclohexanone

To a solution of oxalyl chloride (10.73 g) in dichloromethane (200 ml) was added a solution of dimethyl sulfoxide (14.40 g) in dichloromethane (30 ml) at −60° C., followed by stirring for 5 minutes. To the reaction mixture was added a solution of the compound (17.7 g) obtained in the Reference Example 21 in dichloromethane (75 ml), and after stirring for 15 minutes, triethylamine (38.9 g) was further added dropwise. After stirring for 5 minutes, the temperature was brought up to room temperature over 30 minutes. To the mixture was added water (200 ml) and extraction was carried out with dichloromethane. The extract was dried over anhydrous sodium sulfate and the solvent was evaporated under reduced pressure. The resulting residue was evaporated under reduced pressure to obtain the object compound (16.3 g).

Boiling point: 76° C./0.3mmHg.

IR (KBr): 2955, 2928, 2860, 1720, 1250 cm$^{-1}$ $^1$H-NMR (CDCl$_3$) δ: −0.03 (6H,s , 0.80 9H,s), 1.13–1.95 (8H,m), 1.30(1H,s), 3,40–3.80 (2H,m).

REFERENCE EXAMPLE 23

Production of methyl 3-[4-(tert-butoxycarbonyl)phenyl]acrylate

A solution of tert-butyl 4-formylbenzoate (28.4 g) and methyl (triphenylphosphoranyliden)acetate (46.0 g) in toluene (400 ml) was stirred under heating for 1 hour. The solvent was evaporated under reduced pressure and the resulting residue was purified by column chromatography (support; silica gel, 400 g, developing agent; ethyl acetate: hexane=1:30) to obtain the object compound (27.8 g).

IR (KBr): 2985, 1720, 1710, 1640, 853 cm$^{-1}$ $^1$H-NMR (CDCl$_3$) δ: 1.57(9H,s), 3.79(3H,s), 6.48(1H,d, J=15.5 Hz), 7.55(2H,d,J=8 Hz). 7.68(1H,d,J=15.5 Hz), 7.97(2H,d, J=8 Hz).

REFERENCE EXAMPLE 24

Production of methyl 3-[4-(tert-butoxycarbonyl)phenyl]propionate

The compound (22.5 g) obtained in the Reference Example 23 was dissolved in a mixture of ethyl acetate and methanol (2:1, 300 ml), and thereto was added 10% Pd-C (4.0 g), followed by stirring at room temperature for 4 hours under an atmosphere of hydrogen. The Pd-C was removed off by filtration with celite, and the solvent was evaporated under reduced pressure to obtain the object compound (22.5 g).

IR (Neat): 2980, 1745, 1717, 1610, 850 cm$^{-1}$ $^1$H-NMR (CDCl$_3$) δ: 1.57(9H,s), 2.55(1H,dd,J=6.5 Hz, 1.5 Hz), 2.65(1H,d,J=6.5 Hz), 2.94(H,d,J=6.5 Hz), 3.02(1H,dd, J=6.5 Hz,1.5 Hz), 3.64(3H,s), 7.23(2H,d,J=8 Hz), 7.90(2H,d,J=8 Hz).

REFERENCE EXAMPLE 25

Production of tert-butyl 4-(3-hydroxypropyl)benzoate:

To a solution of the compound (22.8 g) obtained in the Reference Example 24 in dried ether (150 ml) was added lithium boron hydride (2.81 g) at 0° C. The temperature was quickly brought up to room temperature, followed by stirring for 15 hours. To the reaction mixture was added at 0° C. 1N potassium hydrogen sulfate aqueous solution (ca. 125 ml) so that the pH thereof was adjusted to 6.5. After extraction with ether, the ether layer was washed with saturated aqueous sodium chloride and dried over anhydrous sodium sulfate. The solvent was evaporated under reduced pressure to obtain the object compound (20.1 g).

IR (Neat): 3400, 2978, 2935, 1712, 1607, 848 cm$^{-1}$.

$^1$H-NMR (CDCl$_3$) δ: 1.48(1H,s), 1.60(9H,s), 1.70–2.01 (2H,m), 2.73(2H,t,J=6.5 Hz), 3.63(2H,t,J=6.5 Hz), 7.22(2H,d, J=8 Hz), 7.89(2H,d,J-8 Hz).

REFERENCE EXAMPLE 26

Production of tert-butyl 4-(3-bromopropyl)benzoate

To a solution of N-bromosuccinic imide (15.06 g) and triphenylphosphine (22.20 g) in dimethylformamide (100 ml) was added a solution of the compound (10.0 g) obtained in the Reference Example 25 in dimethylformamide (50 ml) at room temperature, followed by stirring for 30 minutes. The temperature was brought up to 50° C., and after stirring for 1 hour, the reaction mixture was poured into ice-water and extracted with ether. The ether layer was washed with water and then saturated aqueous sodium chloride, and dried over anhydrous sodium sulfate. The solvent was evaporated under reduced pressure and the resulting residue was purified by column chromatography (support; silica gel 100 g, developing agent; ethyl acetate : hexane=1:15) to obtain the object compound (11.89 g).

IR (Neat): 2975, 2930, 1710, 1606, 846 cm$^{-1}$.

$^1$H-NMR (CDCl$_3$) δ: 1.58(9H,s), 1.98–2.40(2H,m), 2.82(2H,t,J=7.5 Hz), 3.35(2H,t, J=6 Hz), 7.25(2H,d,J=8 Hz), 7.90(2H,d,J=8 Hz).

REFERENCE EXAMPLE 27

Production of 3-[4-(tert-butoxycarbonyl)phenyl]propyl]triphenylphosphonium bromide A solution of the compound (11.89 g) obtained in the Reference Example 26 and triphenylphosphine (10.41 g) in xylene (50 ml) was heated to 155° C. and stirred for 48 hours. After cooling, the precipitated white crystal was collected by filtration and washed with benzene to obtain the object compound (19.78 g).

IR (KBr): 2975, 2850, 2775, 1710, 1605, 1290, 1110, 856 cm$^{-1}$ $^1$H-NMR (CDCl$_3$) δ: 1.55(9H,s), 1.80–2.13(2H,m), 3.12(2H,t,J=7.5 Hz), 3.70–4.10 (2H,m), 7.25(2H,d,J=8 Hz), 7.50–7.95 (15H,m), 7.83(2H,d,J=8 Hz).

REFERENCE EXAMPLE 28

Production of tert-butyl 4-[3-[4-[(tertbutyldimethylsilyl)oxy]cyclohexylidene]-propyl]benzoate To sodium hydride (0.845 g) was added dimethylsulfoxide (20 ml), and after stirring at 75° C. for one hour, under cooling, thereto was added dropwise a suspension of the compound (19.8 g) obtained in the Reference Example 27 in dimethylsulfoxide (60 ml), followed by stirring at room temperature for 30 minutes. To this suspension was added a solution of the compound (8.06 g) obtained in the Reference Example 22 in dimethylsulfoxide (40 ml), and after stirring at room temperature for 1 hour and at 60° C. for 1 hour, the reaction mixture was poured into ice-water and extracted with ether. The ether layer was washed with water and then saturated aqueous sodium chloride, and dried over anhydrous sodium sulfate. The solvent was evaporated under reduced pressure and the resulting residue was purified by column chromatography (support; silica gel, 200 g, developing agent; ethyl acetate : hexane=1:20) to obtain the object compound (6.11 g).

IR (Neat): 2950, 2930, 2855, 1713, 1605, 1575, 860 cm$^{-1}$ $^1$H NMR (CDCl$_3$) δ: 0.00(6H,s , 0.90(9H,s), 1.10–1.70 (4H,m), 1.59(9H,s), 1.70–2.80 (8H,m), 3.65–3.90(1H,m), 5.10(1H,dt,J=7.5 Hz,1 Hz), 7.20(2H,d,J=8 Hz), 7.87(2H,d,J=8 Hz).

REFERENCE EXAMPLE 29

Production of tert-butyl 4-[3-(4-hydroxycyclohexylidene)propyl]benzoate

To a solution of the compound (6.11 g) obtained in the Reference Example 28 in tetrahydrofuran (30 ml) was added at 0° C. a solution of tetrabutylammonium fluoride (28.4 mmol) in tetrahydrofuran (28.4 ml), and the temperature was brought up to room temperature. After stirring for 16 hours, the reaction mixture was poured into ice-water and extracted with ether. The ether layer was washed with water and then saturated aqueous sodium chloride, and dried over anhydrous sodium sulfate. The solvent was evaporated under reduced pressure and the resulting residue was purified by column chromatography (support; silica gel, 150 g, developing agent; ethyl acetate: hexane=1:4) to obtain the object compound (3.93 g).

IR (Neat): 3390, 2955, 2930, 1710, 1605, 1570, 847 cm$^{-1}$.

$^1$H-NMR (CDCl$_3$) δ: 1.10–1.70(4H,m), 1.60(9H,s), 1.70–2.80(8H,m), 3.60–3.90(1H,m), 5.13(1H,dt,J=7.5 Hz,1 Hz), 7.20(2H,d, J=8 Hz), 7.90(2H,d,J=8 Hz).

REFERENCE EXAMPLE 30

Production of tert-butyl 4-[3-(4-hydroxycyclohexyl)propyl]benzoate

To a solution of the compound (3.90 g) obtained in the Reference Example 29 in ethanol (30 ml) was added 10% Pd-C, followed by stirring at room temperature for 18 hours under an atmosphere of hydrogen. The Pd-C was removed off by filtration with celite and the filtrate was condensed under reduced pressure to obtain the object compound (3.77 g).

IR (Neat): 3380, 2975, 2930, 2853, 1710, 1605, 846 cm$^{-1}$.

$^1$H-NMR (CDCl$_3$) : 0.80–2.15(14H,m), 1.57(9H,s), 2.63(2H,t,J=7.5 Hz), 3.35–3.70 (0.5H,m), 3.85–4.05(0.5H,m), 7.20(2H,d,J=8 Hz), 7.90(2H,d,J=8 Hz).

REFERENCE EXAMPLE 31

Production of tert-butyl 4-[3-(4-oxocyclohexyl)propyl]benzoate

To a solution of oxalyl chloride (1.65 g) in dichloromethane (30 ml) was added a solution of dimethyl sulfoxide (2.21g) in dichloromethane (5 ml) at 60° C., followed by stirring for 5 minutes. To the reaction mixture was added a solution of the compound (3.77 g) obtained in the Reference Example 30 in dichloromethane (10 ml) and after stirring for 15 minutes, thereto was further added dropwise triethylamine (5.97 g). After stirring for 5 minutes, the temperature was brought up to room temperature over 30 minutes, 40 ml of water was added and extraction was carried out with dichloromethane. The dichloromethane layer was washed with water, 0.5N potassium hydrogen sulfate aqueous solution and saturated aqueous sodium chloride in this order, and dried over anhydrous sodium sulfate. The solvent was evaporated under reduced pressure to obtain the object compound (3.60 g) as colorless crystal.

IR (KBr): 2950, 2940, 1720, 1700, 1608, 1290, 1110, 848 cm$^{-1}$.

$^1$H-NMR (CDCl$_3$) δ: 1.20–2.23(9H,m), 1.57(9H,s), 2.23–2.46 (4H,m), 2.66(2H,t,J=7 Hz), 7.22(2H,d,J=8 Hz), 7.90(2H,d,J=8 Hz).

REFERENCE EXAMPLE 32

Production of tert-butyl 4-[3-[3-(ethoxycarbonyl)-4-oxocyclohexyl]propyl]benzoate Under an atmosphere of argon, to a solution of lithium diisopropylamide (1.74 mmol) in tetrahydrofuran (2 ml) was added a solution of the compound (460 mg) obtained in Reference Example 31 in tetrahydrofuran (3 ml) at −78° C., followed by stirring for 30 minutes. To the resulting mixture were added a solution of 1,3-dimethyl-3,4,5,6-tetrahydro-2(1H)pyrimidinone (186 mg) in tetrahydrofuran (1 ml) and a solution of ethyl cyanoformate (172 mg) in tetrahydrofuran (1 ml), and after stirring for 10 minutes, water was added to stop the reaction. Extraction was carried out with ether, and the extract was washed with saturated aqueous sodium chloride and dried over anhydrous magnesium sulfate. The solvent was evaporated under reduced pressure and the resulting residue was purified by column chromatography (support, silica gel, 20 g, developing agent;

ethyl acetate:hexane=1:30) to obtain the object compound (308 mg).

IR (Neat): 2980, 2945, 2865, 1740, 1720, 1710, 1660, 1610 cm$^{-1}$.

$^1$H-NMR (CDCl$_3$) δ: 1.15-1.90 (7H,m), 1.26 (3H,t, J=7 Hz), 1.57 (9H,s), 2.15-2.50 (3H,m), 2.63 (2H,t,j=7 Hz), 4.20 (2H,q,J=7 Hz), 7.20 (2H,d,J=8 Hz), 7 85 (2H,d,j=8 Hz).

WORKING EXAMPLE 1

Production of diethyl N-[4-[3-(2-amino-4-hydroxypyrido[2,3-d]pyrimidin-6-yl)propyl]benzoyl]-L-glutamate Trifluoroacetic acid (30 ml) was added to a solution of the compound (4.67 g) of the Reference Example 6 in dichloromethane (25 ml), followed by stirring at room temperature for 18 hours. To the resulting reaction mixture was dropwise added water (6 ml), followed by stirring for 1 hour. The solvent was evaporated under reduced pressure and to the residue was added ethanol and then benzene. After trifluoroacetic acid was completely removed by azeotropy the resultant was dried at 60° C. under reduced pressure to obtain crude crystals of 4-[3-(2-amino-4-hydroxypyrido[2,3-d]pyrimidin-6-yl)propyl]benzoic acid. Under an atmosphere of argon, to a suspension of the crystals and diethyl glutamate hydrochloride (5.04 g) in dimethylformamide (10 ml), a solution of diphenyl phosphorylazide (5.78 g) in dimethylformamide (15 ml) and a solution of triethylamine (4.27 g) in dimethylformamide (15 ml) were added dropwise at 0° C. The resulting mixture was stirred for 1 hour at 0° C. and then for 66 hours at room temperature. The solvent was evaporated under reduced pressure, and the residue was separated and purified by column chromatography (support:silica gel, 200 g; developing agent:ethyl acetate - ethanol, 9:1→dichloromethane - acetic acid - ethanol, 14:1:1→9:1:1), to obtain the object compound (2.85 g).

IR (KBr): 3250, 2990, 1737, 1720, 1673, 1605, 1595, 1563, 1493 cm$^{-1}$ $^1$H-NMR (DMSO-d$_6$) δ: 1.17 (6H,t,j=7 Hz), 1.70-2.20 (4H,m), 2.20-2.75 (2H,m), 3.00-3.40 (4H,m), 4.00(2H,q,j=7 Hz), 4.08 (2H,q,j=7 Hz), 4.42 (1H,dt, j=7 Hz,7 Hz), 6.60-7.20 (3H,m), 7.30 (2H,d,j=8 Hz), 7.80 (2H,d, j=8 Hz), 8.03 (1H,d,j=3 Hz), 8.40-8.53 (1H,m), 8.60 (1H,d,j=7 Hz).

WORKING EXAMPLE 2

Production of diethyl N-[4-[3-(2-amino-4-hydroxy-5,6,7,8-tetrahydropyrido[2,3-d]pyrimidin-6-yl)propyl]benzoyl]-L-glutamate To a solution of the product (2.28 9) obtained in the Working Example 1 in trifluoroacetic acid (25 ml), 10% Pd-C (50 g: Engelhard Co. Ltd.) was added, followed by vigorous stirring for 16 hours under hydrogen pressure of kg/cm$^2$. The catalyst was removed by filtration, and the filtrate was evaporated under reduced pressure. The resulting residue was purified by column chromatography (support:silica gel, 150 g; developing agent:ethyl acetate→ethyl acetate - ethanol, 10:1 dichloromethane - ethanol, 4:1), to obtain the object compound (2.78 g).

IR (KBr : 3250, 2935, 1720, 1685, 1625, 1545, 800 cm$^{-1}$ $^1$H-NMR (Me2SO-d$_6$) δ:1.10-1.50 (2H,m), 1.23 (3H,t, j=7 Hz), 1.31 (3H,t,j=7 Hz), 1.50-2.00 (5H,m), 2.00-3.00 (7H,m), 3.33 (1H,brd,j=11 Hz), 4.10 (2H, q,j=7 Hz), 4.23 (2H,q,j=7 Hz), 4.60-4.85 (1H,.m), 6.75 (1H,brs), 7.22 (2H,d,j=8 Hz), 7.74 (2H,d, j=8 Hz), 8.35 (2H,brs).

WORKING EXAMPLE 3

Production of diethyl N-[4-[3-(2,4-diaminopyrido[2,3-d]pyrimidin-6-yl)propyl]benzoyl]-L-glutamate The compound (300 mg) obtained in the Reference Example 8 was subjected to the same reaction as that in the Working Example 1, to obtain the object compound (185

IR KBr): 3455, 3330, 3200, 2980, 2935, 1738, 1650, 1613, 1580, 1548 cm$^{-1}$ $^1$H-NMR (CDCl$_3$/CD$_3$OD) δ: 1.23 (3H,t,j=Hz),1.31 (3H,t, j=7 Hz), 1.70-2.82 (10H,m), 4.10 (2H,q,j=7 Hz), 4.22 (2H, q,j=7 Hz), 4.70 (1H,dd, j=8 Hz,6 Hz), 7.21 (2H,d,j=8 Hz), 7.74 (H,d,j=8 Hz), 8.80 (1H,d, j=2 Hz), 8.52 (1H,d,J=2 Hz).

WORKING EXAMPLE 4

Production of diethyl N-[4-[3-(2,4-diamino 5,6,7,8-tetrahydropyrido[2,3-d]pyrimidin-6-yl)propyl)-benzoyl]-L-glutamate The compound (124 mg) obtained in the Working Example was subjected to the same reaction as that in the Working Example 2, to obtain the object compound (112 mg).

IR (KBr): 3392, 3220, 2940, 1740, 1640, 1610, 1580, 1538, 1505, 1445 cm$^{-1}$ $^1$H-NMR (CDCl$_3$) δ: 1.20-3.15 (14H,m), 1.21 (3H,t, j=7 Hz), 1.30 (3H,t,j=7 Hz), 3.30 (1H,brd,j=11 Hz), 4.10 (2H,q,j=7 Hz), 4.23 (2H,q,j=7 Hz), 4.45 (5H,brs), 4.65-4.90 (1H,m), 4.93 (1H,d, j=3 Hz), 7.13 (1H,d,j=7 Hz), 7.25 (2H,d,j=8 Hz), 7.73 (2H,d,j=8 Hz).

WORKING EXAMPLE 5

Production of diethyl N-[4-[3-(2-amino-4-hydroxy-5-methylpyrido[2,3-d]pyrimidin-6-yl)propyl]benzoyl]-L-glutamate The compound (590 mg) obtained in the Reference Example 13 was subjected to the same reaction as that in the Working Example 1, to obtain the object compound (306 mg).

IR (Neat): 3250, 2925, 1737, 1700, 1633 cm$^{-1}$ $^1$H-NMR (DMSO-d$_6$/TFA-d) δ: 1.20 (3H,t,j=7 Hz), 1.60-2.20 (4H,m), 2.30-3.30 (6H,m), 2.78 (3H,s), 4.05 (2H,q,j=7 Hz), 4.13 (2H,q, j=7 Hz), 4.33-4.56 (1H,m), 7.27 (2H,d,j=8 Hz), 7.83 (2H,d,j=8 Hz), 8.37 (1H,s).

WORKING EXAMPLE 6

Production of diethyl N-[4-[3-(2-amino-4-hydroxy-5,6,7,8-5-methyl-tetrahydro-pyrido[2,3-d]pyrimidin-6-yl)propyl]benzoyl]-L-glutamate The compound 416 mg) obtained in the Working Example was subjected to the same reaction as that in the Working Example 2, to obtain the object compound (150 mg).

IR (KBr): 3350, 2930, 1730, 1685, 1633, 1615, 1540 cm$^{-1}$ $^1$H-NMR (CDCl$_3$CD$_3$OD) : 0.87 (3H,d,]=7 Hz), 1.10-1.90 (6H.,m), 1.22 (3H,t,j=7 Hz), 1.30 (3H,t,j=7 Hz), 1.95-3.00 (8H,m), 3.10(4H,brs), 4.10 (2H,q,j=7 Hz), 4.23 (2H,q, j=7 Hz), 4.67-4.90 (1H,m), 7.22 (2H,d,j=8 Hz), 7.46 (1H,d, j=8.5 Hz), 7.73 (2H,d,j=8 Hz).

WORKING EXAMPLE 7

Production of diethyl N-[4-[3-(2-amino-4-hydroxypyrido[2,3-d]pyrimidin-6-yl)-1-methylpropyl]benzoyl]-L-glutamate:

The compound (2.15 g) obtained in the Reference Example 20 was subjected to the same reaction as that in the Working Example 1, to obtain the object compound (1.51 g).

$^1$H-NMR (DMSO-$d_6$/TFA-d) δ: 1.19 (6H,t,j=7.5 Hz), 1.22 (3H,d,j=7 Hz), 1.50-2.25 (4H,m), 2.30-3.10 (5H,m), 4.06 (2H,q,j=7.5 Hz), 4.12 (2H,q,]=7.5 Hz , 4.35-4.62 (1H,m), 7 42 (2H,d,j=8 Hz), 7.85 (2H,d,j=8 Hz), 8.41 (1H,d,j=2 Hz), 8.51 (1H,d, j=2 Hz).

WORKING EXAMPLE 8

Production of diethyl N-[4-[3-(2-amino-4-hydroxy-5,6,7,8-tetrahydropyrido[2,3-d]pyrimidin-6-yl)-1-methylpropyl]benzoyl]-L-glutame The compound (230 mg) obtained in the Working Example was subjected to the same reaction as that in the Working Example 2, to obtain the object compound (232 g).

IR (KBr): 3370, 2930, 1720, 1685, 1640, 1610, 1548 cm$^{-1}$ $^1$H-NMR (CDCl$_3$/CD$_3$OD) δ:1.00-1.40 (2H,m), 1.22 (3H,t, j=7 Hz), 1.31 (3H,t,]=7 Hz), 1.45-2.00 (4H,m), 2.00-3.00 (7H,m), 3.23 (4H,brd,j=11 Hz), 4.12 (2H,q,j=7 Hz), 4.23 (2H,q, j=7 Hz), 4.63-4.76 (1H,m),7.22 (2H,d,j=8 Hz), 7.74 (2H,d, j=8 Hz).

WORKING EXAMPLE 9

Production of N-[4-[3-(2-amino-4-hydroxypyrido[2,3-d]pyrimidin-6-yl)propyl]benzoyl]-L-glutamic acid The diethyl ester (100 mg) obtained in the Working Example 1 was dissolved in hydrated tetrahydrofuran (1:1:, 10 ml). To the resulting solution was added 1N sodium hydroxide aqueous solution (1.7 ml) and hydrolysis was carried out at room temperature for 18 hours. Insoluble hydroxide aqueous solution (1.7 ml) and hydrolysis was carried out at room temperature for 18 hours. Insoluble matter was removed by filtration and to the filtrate added acetic acid (1.7 ml). The resulting mixture was concentrated to 1 ml under reduced pressure, followed by addition of water (2 ml) to yield white crystals. The crystals were collected by filtration, washed with ice water and dried, to obtain the object compound (60 mg).

IR (KBr): 3500-2300, 1705, 1665, 1600, 802 cm$^{-1}$ $^1$H-NMR (TFA-d) δ: 1.95-2.36 (4H,m), 2.36-2.70 (2H,m), 2.70-3.10 (4H,m), 5.10 (1H,dd, j=8 Hz,5 Hz), 7.40 (2H,d,j=8 Hz), 7.82 (2H,d,j=8 Hz), 8.63 (1H,brs), 8.96 (1H,d,]=2 Hz)

WORKING EXAMPLE 10

Production of N-[4-[3-(2-amino-4-hydroxy-5,6,7,8-tetrahydropyrido[2,3-d]pyrimidin-6-yl)propyl]benzoyl]-L-glutamic acid The diester (2.78 g) obtained in the Working Example 2 was hydrolyzed in the same manner as that in the Working Example 9, to obtain the object compound (1.20 g).

IR (KBr): 3350, 2930, 1710, 1660, 1640 cm$^{-1}$ $^1$H-NMR (Me$_2$SO-$d_6$) δ: 1.00-1.45 (2H,m), 1.45-1.80 (4H,m), 1.80-2.20 (2H,m), 2.20-2.90 (6H,m), 3.15 (1H,brd, J=12 Hz), 4.40 (1H,dt,J=8 Hz, 8 Hz), 5.90 (2H,brs), 6.18 (1H,brs), 7.32 (2H,d,J=8 Hz), 7.83 (2H,d,J=8 Hz), 8.50 (1H,d,J=8 Hz).

WORKING EXAMPLE 11

Production of N-[4-[3 (2,4-diaminopyrido[2,3-d]pyrimidin-6-yl)propyl]benzoyl]-L-glutamic acid The compound (50 mg) obtained in the Working Example 3 was subjected to the same reaction as that in the Working Example 9, to obtain the object compound (42 mg).

IR (KBr): 3350, 3200, 2945, 1640, 1597, 1540, 1505, 1400, 800 cm$^{-1}$ $^1$H-NMR (DMSO-$d_6$) δ: 1.75-2.20 (4H,m), 2.20-2.43 (2H,m), 2.45-2.83 (6H,m), 4.25-4.54 (1H,m), 7.13 (2H,brs), 7.31 (2H,d,J=8 Hz), 7.83 (2H,d,J=8 Hz), 7.88 (2H,brs), 8.31 (1H,brs), 8.41 (1H,brs), 8.55 (1H,brs).

WORKING EXAMPLE 12

Production of N-[4-[3-(2,4-diamino-5,6,7,8-tetrahydropyrido[2,3-d]pyrimidin-6-yl)propyl]benzoyl]-L-glutamic acid The compound (100 mg) obtained in the Working Example 4 was subjected to the same reaction as that in the Working Example 9, to obtain the object compound (74 mg).

IR (KBr): 3350, 3240, 2940, 1650, 1565, 1503, 1400, 762 cm$^{-1}$ $^1$H-NMR (DMSO-$d_6$) : 1.10-1.48 (2H,m), 1.50-3.05 (12H,m), 3.23 (1H,brd,J=12 Hz), 4.16-4.45 (1H,m), 6 66 (4H, brs), 7.21 (1H,brs), 7.27 (2H,d,J=8 Hz), 7.80 (H,d,J=8 Hz), 8.20 (1H,d,J=7 Hz).

WORKING EXAMPLE 13

Production of N-[4-[3-(2-amino 4-hydroxy-5-methylpyrido[2,3-d]pyrimidin-6-yl)propyl]benzoyl]-L-glutamic acid The compound (56 mg) obtained in the Working Example 5 was subjected to the same reaction as that in the Working Example 9, to obtain the object compound (31 mg).

IH (KBr): 350-2300, 1700, 1650 cm$^{-1}$ $^1$H-NMR (DMSO-$d_6$/TFA-d) δ: 1.60-2.16 (4H,m), 2.30 (2H,d,J=6.5 Hz), 2.35-2.90 (4H,m), 2.73 (3H,s), 4.23-4.50 (1H,m), 7.28 (2H,d,J=8 Hz), 7.80 (2H,brd,J=8 Hz), 8.33 (1H,s).

WORKING EXAMPLE 14

Production of N-[4-[3-(2-amino-4-hydroxy-5-methyl-5,6,7,8-tetrahydropyrido[2,3-d]pyrimidin-6-yl)propyl]-benzoyl]-L-glutamic acid The compound (75 mg) obtained in the Working Example 6 was subjected to the same reaction as that in the Working Example 9, to obtain the object compound (37 mg).

IR KBr : 3340, 2920, 1700, 1640, 1540 cm$^{-1}$ $^1$H-NMR (DMSO-$d_6$) δ:0.74 (3H,d,J=7 Hz), 1.00-1.35 (2H,m), 1.35-1.80 (4H,m), 1.80-2.20 (2H,m), 2.20-2.90 (6H,m), 4.23-4.56 (1H,m), 5.95 (2H, brs), 6.25 (1H,brs), 7.30 (2H,d,J=8 Hz), 7.82 (2H,d, J=8 Hz), 7.48 (1H,d,J=7.5 Hz).

WORKING EXAMPLE 15

Production of N-[4-[3-(2-amino 4-hydroxypyrido[2,3-d]pyrimidin-6-yl)-1-methylpropyl]benzoyl]-L-glutamic acid The compound (65 mg) obtained in the Working Example 7 was subjected to the same reaction as that in the Working Example 9, to obtain the object compound (38 mg).

IR (KBr): 3500–2300, 1697, 1675 cm$^{-1}$ $^1$H-NMR (DMSO-d$_6$/TFA-d) : 1.27 (3H,d,J=7 Hz), 1.70–2.23 (4H m), 2.25–2.98 (5H,m), 4.33 4.60 (1H,m), 7.33 (2H,d,J=8 Hz , 7.87 (2H,d,J=8 Hz), 8.43 (1H, d,J=1.5 Hz), 8.49 (1H,d, J=1.5 Hz).

WORKING EXAMPLE 16

Production of N-[4-[3-(2-amino-4-hydroxy-5,6,7,8-tetrahydropyrido[2,3-d]pyrimidin-6-yl)-1-methylpropyl]-benzoyl]-L-glutamic acid The compound (232 mg) obtained in the Working Example 8 was subjected to the same reaction as that in the Working Example 9, to obtain the object compound (102 mg).

IR (KBr): 3345, 2925, 1700, 1640, 1540 cm$^{-1}$ $^1$H-NMR (DMSO-d$_6$) δ: 1.00–1.40 (2H,m), 1.21 (3H,d,J=6 Hz), 1.40 2.80 (11H,m), 3.30 (1H,brd,J=12 Hz), 4.23–4.56 (1H,m), 5.92 (2H,brs), 6.20 (1H,brs), 7.27 (2H,d,J=8 Hz), 7.73 (2H,d,J=8 Hz), 8.43 (1H,d,J=8 Hz).

WORKING EXAMPLE 17

Production of tert-butyl 4-[3-(2,4-diamino-5,6,7,8-tetrahydroquinazolin-6-yl)propyl]benzoate A mixture of the compound (316 mg) obtained in the Reference Example 31 and dicyanodiamide (126 mg) was heated at 180° C. for 4 hours, and the resulting blackish brown oil was purified by column chromatography (support:silica gel, 15 g, developing agent; dichloromethane:methanol=12:1→7:1) to obtain the object compound (78 mg).

IR (KBr): 3480, 3340, 3160, 2950, 1718, 1640, 1610, 1590, 1573, 1450, 1293, 1170, 1115, 1020, 850 cm$^{-1}$ $^1$H-NMR (CDCl$_3$) δ: 1.20–2.50 (9H,m), 1.58 (9H,s), 2.50–2.80 (4H,m), 4.80 (4H,brs), 7.18 (2H,d,j=8 Hz), 7.89 (2H,d, j=8 Hz).

WORKING EXAMPLE 18

Production of diethyl N-[4-[3-(2,4-diamino-5,6,7,8-tetrahydroquinazolin-6-yl)propyl]benzoyl]-L-glutamate To the compound (70 mg) obtained in the Working Example 17 was added trifluoroacetic acid (1 ml), followed by stirring at room temperature for 2 hours. The solvent was evaporated under reduced pressure and the residue was dried under a vacuum at 70° C. to obtain crude crystal of 4-[3-(2,4-diamino-5,6,7,8-tetrahydroquinazolin-6-yl)propyl]benzoic acid. To a solution of this crystal and diethyl L-glutamate hydrochloride (132 mg) in dimethylformamide (0.5 ml) was added, under an atmosphere of argon and at 0° C., a solution of diphenyl phosphorylazide (116 mg) in dimethylformamide (0.5 ml), followed by stirring for 15 minutes and thereto was added dropwise at the same temperature a solution of triethylamine (93 mg) in dimethylformamide (0.5 ml). After stirring at 0° C. for 30 minutes and then at room temperature for 72 hours, the solvent was evaporated under reduced pressure and the resulting residue was purified by column chromatography (support; silica gel, 10 g, developing agent; dichloromethane separated from conc. aqueous ammonia dichloro methane separated from conc. aqueous ammonia:ethanol=20:1) to obtain the object compound (82 mg) as a white crystal.

IR (KBr): 3448, 3350, 3130, 2948, 1738, 1660, 1635, 1630, 1570, 1445, 1200, 1020 cm$^{-1}$ $^1$H-NMR (CDCl$_3$) : 1.23 (3H,t,j=7 Hz), 1.31 (3H,t, j=7 Hz), 1.33–1.50 (3H,m), 1.66–1.83 (3H,m), 1.83–2.01 (2H,m), 2.03–2.52 (5H,m), 3.60 (2H,dd,j=9 Hz,4 Hz), 3.70 (2H,t,j=7 Hz), 4.12 (2H,q, j=7 Hz), 4.25 (2H,q,j=7 Hz), 4.58 (2H,brs), 4.62 (2H,brs), 4.75–4.88 (1H,m), 7.03 (1H,d,j=8.5 Hz), 7.26 (2H,d,j=8 Hz), 7.76 (2H,d,j=8 Hz).

WORKING EXAMPLE 19

Production of N-[4-[3-(2,4-diamino-5,6,7,8-tetrahydroquinazolin-6-yl)propyl]benzoyl]-L-glutamic acid To a solution of the compound (77 mg) obtained in the Working Example 18 in a mixture of tetrahydrofuran - water (3:2, 2.5 ml) was added 1N sodium hydroxide aqueous solution (0.76 ml), and after stirring at room temperature for 2 hours, the supernatant was removed by filtration with milipore filter. To the filtrate was added acetic acid (0.5 ml), and the resultant was concentrated up to ca. 1 ml by evaporation of the solvent under reduced pressure, followed by addition of water (5 ml) with irradiation of supersonic waves to give a white crystal. This crystal was collected by filtration, washed sufficiently with ice-water and dried at 60° C. under reduced pressure to obtain the object compound (64 mg).

IR (KBr): 3350, 3200, 2935, 1710, 1660, 1650, 1640, 1530, 1500, 1400 cm$^{-1}$ $^1$H-NMR (Me$_2$SO-d$_6$) δ: 1.10–1.45 (3H,m), 1.50–2.17 (8H,m), 2.20–2.50 (4H,m), 2.55–2.73 (2H,m), 3.00–5.10 (4H,m), 4.29 (1H,dd,j=7 Hz,6.5 Hz), 7.08 (1H,brs), 7.28 (2H,d,J=8 Hz), 7.30 (1H,brs), 7.78 (2H,d, J=8 Hz), 8.27 (1H,d,j=6.5 Hz).

WORKING EXAMPLE 20

Production of tert-butyl 4-[3-(2-amino-4-hydroxy-5,6,7,8-tetrahydroquinazolin-6-yl)propyl]benzoate Under an atmosphere of argon, to a solution of potassium tert-butoxide (86 mg) and guanidine hydrochloride (79.5 mg) in tert-butyl alcohol (2 ml) was added a solution of the compound (308 mg) obtained in the Reference Example 32 in tert butyl alcohol (4 ml), followed by heating under reflux for 3 hours. The reaction mixture was cooled and poured into ice-water, and the resulting crystal was collected by filtration and washed with acetone and then ether to obtain the object compound (263 mg).

IR (KBr): 3320, 3080, 2980, 2940, 1708, 1670, 1650, 1605, 1495, 1367, 1290, 1168, 1118, 1108, 1013, 848 cm$^{-1}$ $^1$H-NMR (Me$_2$SO-d$_6$-CD$_3$COOD) δ: 1.20–1.40 (3H,m), 1.50–1.85 (6H,m), 1.55 (9H,s), 2.30–2.48 (2H,m), 2.68 (2H,t,j=7 Hz), 7.33 (2H,d, j=8 Hz), 7.84 (2H,d, j=8 Hz).

WORKING EXAMPLE 21

Production of diethyl N-[4-[3-(2-amino-4-hydroxy-5,6,7,8-tetrahydroquinazolin-6-yl)propyl]benzoyl]-L-glutamate In the same manner as in the Working Example 18, from the compound (250 mg) obtained in the Working Example 20 was obtained the object compound (132 mg) as a white crystal.

IR (KBr): 3390, 3165, 2940, 1738, 1660, 1650, 1640, 1608, 1525, 1503, 1390, 1180, 1095, 1120, 853 cm$^{-1}$ $^1$H-NMR (Me$_2$SO-d$_6$) δ: 1.16 (3H,t,j=7 Hz), 1.19 (3H,t, j=7 Hz), 1.25-1.38 (2H,m), 1.40-2.20 (7H,m), 2.25-2.45 (6H,m), 2.65 (2H,t,j=6.5 Hz), 4.05 (2H,q,j=7 Hz), 4.12 (2H,q,j=7 Hz), 4.37-4 50 (1H,m), 6.19 (2H,brs), 7.32 (2H,d,j=8 Hz), 7.81 (2H,d, j=8 Hz), 8.66 (1H,d,j=7.5 Hz).

WORKING EXAMPLE 22

Production of N-[4-[3-(2-amino-4-hydroxy-5,6,7,8-tetrahydroquinazolin-6-yl)propyl]benzoyl]-L-glutamic acid In the same manner as in the Working Example 19, from the compound (130 mg) obtained in the Working Example 21 was obtained the object compound (106 mg).

IR (KBr): 3360, 3185, 2930, 1705, 1607, 855, 820 cm$^{-1}$ $^1$H-NMR (Me$_2$SO-d$_6$) : 1.15-1.40 (3H,m), 1.40-1.86 (5H,m), 1.86-2.20 (2H,m), 2.24-2.50 (5H,m), 2.65 (2H,t,j=7 Hz), 4.32-4.47 (1H,m), 6.20 (2H,brs), 7.31 (2H,d,j=8 Hz), 7.81 (2H,d, j=8 Hz), 8.53 (1H,d,j=8 Hz).

WORKING EXAMPLE 23

Production of tert-butyl 4-[3-(2,4-diaminoquinazolin-6-yl)propyl]benzoate

The compound 200 mg obtained in the Working Example was dissolved in 1,4-dioxine (3 ml), and the mixture was refluxed by heating in the presence of 10% Pd-C (200 mg) for 7 days. After removing the catalyst by filtration with celite, the filtrate was concentrated to dyness under reduced pressure. The residue was purified by column chromatography (support; silica gel, 20 g, developing agent; dichloromethane:methanol=7:1) to obtain the object compound (79 mg).

IR (KBr): 3470, 3350, 2950, 1718, 1640, 1610, 1590, 848 cm$^{-1}$ $^1$H-NMR (CDCl$_3$) δ: 1.59 (9H,s), 1.90-2.05 (2H,m), 2.60-2.80 (4H,m), 4.63 (2H,brs), 5.27 (2H,brs), 7.19 (2H,d,j=8 Hz), 7.28-7.39 (1H,m), 7.53-7.63 (1H,m), 7.85-7.93 (1H,m).

WORKING EXAMPLE 24

Production of diethyl N-[4-[3-(2,4-diaminoquinazolin-6-yl)propyl]benzoyl]-L-glutamate In the same manner as in the Working Example 18, from the compound (79 mg) obtained in the Working Example 23 was obtained the object compound (79 mg).

IR (KBr): 3448, 3350, 2950, 1735, 1660, 1630, 1570 cm$^{-1}$ $^1$H-NMR (CDCl$_3$) δ: 1.23 (3H,t,j=7 Hz), 1.31 (3H,t, j=7 Hz), 1.93-2.19 (4H,m), 2.44 (2H,t,j=6 Hz), 2.58-2.82 (4H,m), 4.12 (2H,q,]=7 Hz), 4.25 (2H,q,j=7 Hz), 4.62 (2H,brs), 4.75-4.88 (1H,m), 4.95 (2H,brs), 7.26 (2H,d,j=8 Hz), 7.28-7.45 (2H,m), 7.53-7.63 (1H,m), 7.76 (2H,d,j=8 Hz), 7.85-7.93(1H,m).

WORKING EXAMPLE 25

Production of N-[4-[3-(2,4-diaminoqinazolin-6-yl)propyl]benzoyl]-L-glutamic acid In the same manner as the Working Example 19, from the compound (79 mg) obtained in the Working Example 24 was obtained the object compound (63 mg).

IR (KBr): 3350, 3200, 2930, 1708, 1660, 1638, 1530 cm$^{-1}$ $^1$H-NMR (Me$_2$SO-d$_6$) δ: 1.75-2.20 (4H,m), 2.40 (2H,t,j=7 Hz), 2.60-2.80 (4H,m), 3.20-4.50 (4H,m), 4.39 (1H,dd, j=7 Hz,6 Hz), 7.30 (2H,d,j=8 Hz), 7.30-7.40 (1H,m), 7.50-7.65 (1H,m), 7.82 (2H,d,j=8 Hz), 7.85-7.93 (1H,m), 8.48 (1H,d,j=6 Hz).

WORKING EXAMPLE 26

Production of tert-butyl 4-[3-(2-amino-4-hydroxyquinazolin-6-yl)propyl]benzoate

In the same manner as the Working Example 23, from the compound (200 mg) obtained in the Working Example 20 was obtained the object compound (73 mg).

IR (KBr): 3325, 3075, 2975, 2945, 1710, 1675, 1650, 1600, 1495, 848 cm$^{-1}$ $^1$H-NMR (Me$_2$SO-d$_6$-CD$_3$COOD) δ: 1.59(9H,s), 1.90-2.05 (2H,m), 2.60-2.85 (4H,m), 7.25-7.42 (1H,m), 7.32 (2H,d,j=8 Hz), 7.50-7.65 (1H,m), 7.85-7.95 (1H,m), 7.85 (2H,d,j=8 Hz).

WORKING EXAMPLE 27

Production of diethyl N-[4-[3-(2-amino-4-hydroxyquinazolin-6-yl)propyl]-benzoyl-L-glutamate In the same manner as in the Working Example 18, from the compound (73 mg) obtained in the Working Example 26 was obtained the object compound (80 mg).

IR (KBr): 3395, 3170, 2945, 1740, 1663, 853 cm$^{-1}$ $^1$H-NMR (Me$_2$SO-d$_6$) δ: 1.16 (3H,t,j=7 Hz), 1.19 (3H,t,j=7 Hz), 1.90-2.20 (4H,m), 2.20-2.50 (2H,m), 2.55-2.85 (4H,m), 4.05 (2H,q,j=7 Hz), 4.12 (2H,q,j=7 Hz), 4.35-4.53 (1H,m), 6.10 (2H,brs), 7.29 (2H,d, j=8 Hz), 7.30-7.43 (1H,m), 7.50-7.60 (1H,m), 7.80 (2H,d,j=8 Hz), 7.85-7.93 (1H,m), 8.54 (1H,d, j=7.5 Hz).

WORKING EXAMPLE 28

Production of N-[4-[3-(2-amino-4-hydroxyquinazolin-6-yl)prolpyl]-benzoyl]-L-glutamic acid In the same manner as the Working Example 19, from the compound (80 mg) obtained in the Working Example 27 was obtained the object compound (62 mg).

IR (KBr): 3360, 3180, 2925, 1710, 1605, 850 cm$^{-1}$ $^1$H-NMR (Me$_2$SO-d$_6$) δ: 1.70-2.20 (4H,m), 2.60-2.80 (4H,m), 2.64 (2H,t,j=7 Hz), 4.30-4.42 (1H,m), 6.29 (2H,brs), 7.30 (2H,d,j=8 Hz), 7.32-7.40 (1H,m), 7.55-7.65 (1H,m), 7.82 (2H,d, j=8 Hz), 7.85-7.93 (1H,m), 8.58 (1H,d,j=7 Hz).

WORKING EXAMPLE 29

The compound (50 mg for preparation of a tablet) obtained in the Working Example 12, lactose (250 mg for preparation of a tablet), corn starch (51 mg for preparation of a tablet) and Hydroxypropylcellulose L (9 mg for preparation of a tablet) were mixed and granulated by the conventional means. The obtained granules were mixed with corn starch (8 mg for preparation of a tablet) and magnesium stearate (2 mg for preparation of a tablet), followed by tabletting according to the conventional manner to give tablets (370 mg for preparation of a tablet).

WORKING EXAMPLE 30

In 1 l of physiological saline was dissolved 10 g of sodium salt of the compound obtained in the Working Example 11, and after filtration with microfilter 2.2 ml portions of the filtrate were poured and sealed in an ampoule. The ampoule was sterilized at 110° C. for 30 minutes, to obtain an ampoule for subcutaneous, intravenous or intramuscular injection of said compound.

WORKING EXAMPLE 31

In 1 l of distilled water were dissolved 5 g of hydrochloric acid salt of the compound obtained in the Working Example 12 and 10 g of mannitol, and after sterilization and filtration, 2 ml portions of the filtrate were poured into an ampoule. The ampoule was freeze-dried and sealed in a freeze-drier, to obtain an ampoule for use with contemporary dissolution of the content. For use, the ampoule is opened and the content is dissolved in, for example, 2 ml of physiological saline to obtain a prepared injection.

What we claim is:

1. A compound of the formula:

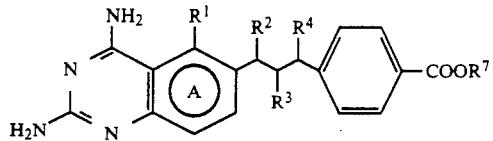

wherein the ring (A) is condensed with the pyrimidine ring to form a pyrido[2,3-d]pyrimidine or 5,6,7,8-tetrahydro-pyrido[2,3-d]pyrimidine group, $R^1$, $R^2$, $R^3$ and $R^4$ are independently hydrogen fluorine or a lower alkyl group, and $R^7$ is (i) hydrogen, (ii) $C_{1-6}$alkyl, (iii) a benzyl group which may be substituted with one or two substituents selected from the group consisting of nitro and $C_{1-3}$alkoxy or (iv) a phenyl group which may be substituted with 1 or 2 substituents selected from the group consisting of nitro and $C_{1-3}$alkoxy, or a salt thereof.

* * * * *

UNITED STATES PATENT AND TRADEMARK OFFICE
CERTIFICATE OF CORRECTION

PATENT NO. : 5,223,620
DATED : June 29, 1993
INVENTOR(S) : Hiroaki NOMURA et al.

It is certified that error appears in the above-indentified patent and that said Letters Patent is hereby corrected as shown below:

Column 40 (CLAIM 1), line 18, "hydrogen fluorine or a lower alkyl" should be --hydrogen, fluorine or a lower alkyl--

Signed and Sealed this

Third Day of May, 1994

Attest:

BRUCE LEHMAN

*Attesting Officer*  *Commissioner of Patents and Trademarks*